United States Patent
Fowlie et al.

(10) Patent No.: US 9,386,770 B2
(45) Date of Patent: Jul. 12, 2016

(54) USE OF PREDISSOLVED PRISTINAMYCIN-TYPE AND POLYETHER IONOPHORE TYPE ANTIMICROBIAL AGENTS IN THE PRODUCTION OF ETHANOL

(75) Inventors: David Alan Fowlie, Concord, NC (US); Wayne Mattsfield, Lakeville, MN (US); Dennis P. Bayrock, Rosemount, MN (US)

(73) Assignee: Phibro Animal Health Corp., Teaneck, NJ (US)

( * ) Notice: Subject to any disclaimer, the term of this patent is extended or adjusted under 35 U.S.C. 154(b) by 1288 days.

(21) Appl. No.: 13/067,385

(22) Filed: May 27, 2011

(65) Prior Publication Data

US 2011/0294725 A1 Dec. 1, 2011

Related U.S. Application Data

(63) Continuation-in-part of application No. 11/806,591, filed on Jun. 1, 2007.

(60) Provisional application No. 61/344,152, filed on Jun. 1, 2010, provisional application No. 60/812,965, filed on Jun. 13, 2006.

(51) Int. Cl.
| | |
|---|---|
| *A01N 63/02* | (2006.01) |
| *A01N 37/18* | (2006.01) |
| *A01N 43/90* | (2006.01) |
| *C12P 7/06* | (2006.01) |

(52) U.S. Cl.
CPC ............ *A01N 43/90* (2013.01); *A01N 63/02* (2013.01); *C12P 7/06* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 2004/0208906 | A1* | 10/2004 | Tatara et al. | 424/401 |
| 2008/0003215 | A1* | 1/2008 | Bayrock | 424/115 |

* cited by examiner

*Primary Examiner* — Jeanette Lieb
(74) *Attorney, Agent, or Firm* — Christopher G. Hayden; Hayden Stone PLLC

(57) ABSTRACT

A method of controlling microorganisms such as *lactobacilli* metabolism in mash in an ethanol production facility includes adding to the mash an effective amount to control such microorganisms of one or more of a substantially water insoluble pristinamycin-type antimicrobial agent, a substantially water insoluble polyether ionophore antimicrobial agent, or both, wherein the term "substantially water insoluble" means the antimicrobial agent has a solubility in pure water at 20° C. of 0.1 grams per liter or less, and wherein at least a portion of the substantially water insoluble antimicrobial agent(s) is added to the mash in the form of: 1) an organic liquid comprising at least one organic solvent having said substantially water insoluble antimicrobial agent(s) dissolved therein, said organic liquid advantageously comprising more than 1 gram per liter of said antimicrobial agent(s); 2) particles comprising said substantially water insoluble antimicrobial agent(s) and having a weight mean average diameter of less than 5 microns; or 3) both.

20 Claims, No Drawings

USE OF PREDISSOLVED PRISTINAMYCIN-TYPE AND POLYETHER IONOPHORE TYPE ANTIMICROBIAL AGENTS IN THE PRODUCTION OF ETHANOL

CROSS-REFERENCE TO RELATED APPLICATIONS

This application claims priority to U.S. Provisional application No. 61/344,152 filed Jun. 1, 2010, titles Use Of predissolved pristinamycin-type and polyether type antimicrobial agents in the production of ethanol, and also claims priority to U.S. Provisional application No. 60/812,965 filed Jun. 13, 2006, and also claims priority as a continuation-in-part to application Ser. No. 11/806,591 filed on Jun. 1, 2007, the entire documents of which are incorporated by reference herein for all allowable purposes.

BACKGROUND OF THE INVENTION

Ethanol production through anaerobic fermentation of a carbon source by the yeast *Saccharomyces cerevisiae* is one of the best known biotechnological processes and accounts for a world production of more than 35 billion liters per year. Two-thirds of the production is located in Brazil and in the United States with the primary objective of using ethanol as a renewable source of fuel. Hence, there are strong economic incentives to further improve the ethanol production process. The price of the sugar source or carbohydrate source is a very important process parameter in determining the overall economy of ethanol production. Using unaltered yeasts, the greatest yield obtainable is only about 51.1%, with the remainder being lost to yeast maintenance and growth, glycerol production, and other end products. The typical ethanol yield is lower than the above-described maximum theoretical yield in large part due to competing microorganisms.

A typical ethanol production plant comprises a premixing vessel where water and the carbohydrate fuel source (hereafter referred to as mash) are held at 40° C. to 60° C. and where (if corn is the source of carbohydrate) a small amount of enzyme such as a-amylase is added. The mash is then heated to between 90° C. to 150° C. for a period of time, and then cooled and held between 80° C. to 90° C. as the mash liquefies. The mash is then cooled to 60° C. and additional enzymes may be added in a saccharification step. After a period of time at 60° C., the mash is cooled to ambient to ~35° C., and the liquid is then sent to fermentors where yeast is added to convert sugars to ethanol. In a continuous process utilization of a number of serially linked fermentors is typical, as this is required for efficient conversion of the sugars and also because ethanol-production-favorable conditions (which depend on the amount of alcohol and other byproducts present in the mash) can be optimized.

The economic viability of the ethanol production process, and indeed whether the process results in positive production of fuel source, depends to a large extent on the recovery and re-use of the latent heat of the mash. This recovery and re-use of heat energy is performed by use of heat exchangers, which are typically installed in the process to maximize the recovery of high quality heat. A substantial problem faced by the industry is that in certain units, for example where mash is held at 90° C. to 150° C., most antimicrobial agents added to the mash would be inactivated and destroyed by the heat. In liquefaction and saccharification units operating at 90° C., this is only a minor problem as *lactobacilli* and other microorganisms cannot thrive at those temperatures. However, *lactobacilli* and other microorganisms can colonize and thrive in the heat exchangers held at lower temperatures at the exit of the higher temperature units. There is no practical method, using powdered antimicrobial agents, of providing an active concentration of the antimicrobial agent to mash passing through heat exchangers immediately following units operated at high temperatures. Antimicrobial agents added to units is largely inactivated by heat, and the kinetics of dissolution of these antimicrobial agents are too slow to provide an effective concentration of these antimicrobial agents in the time frame where the mash passes through the heat exchangers, so effective control of *lactobacilli* and other microorganisms in these first heat exchangers is not readily achieved using the most effective current antimicrobial products (pristinamycin-type antimicrobial agents, polyether ionophore-type antimicrobial agents, or both). In one aspect of this invention, use of presolubilized pristinamycin-type antimicrobial agents, polyether ionophore-type antimicrobial agents, or both, injected (by batch, pulse, or continuous means) immediately upstream of or even within the body of the heat exchangers, solves this problem.

Finally, the fermented mash (containing corn particles, alcohol, and water) is sent to a distilling column where alcohol is extracted, and the dried residual material find large markets in the animal feed business as DDG.

Large volumes are processed, and as one might imagine with all the temperature changes involved in the process that heat exchangers are critical to both net production of energy and to the economics of the process. Bacterial slime will impair heat exchanger efficiency. Similar use can be made in other areas of the plant, and in other unit operations in plants having different configurations, where there is a need to provide in a short period of time an effective concentration of pristinamycin-type antimicrobial agents, polyether ionophore-type antimicrobial agents, or both.

One particularly difficult problem is the control of competing microorganisms, in particular bacteria of the LAB (Lactic Acid Bacteria family) which encompasses many bacterial species of similar growth and physiological traits. One example is *Lactobacillus paracasei* which compete with the yeast for nutrients and produce lactic acid. Other microorganisms such as *Acetobacter/Gluconobacter* and wild yeasts must also be controlled. Since control of LAB is critical to the process viability and since control of one class of microorganisms by the methods described here results in control of at least some of the other microorganisms, this discussion will focus on LAB control. One of skill in the art will know that a number of other competing microorganisms will also be controlled by the treatment processes described here, depending on the antibiotics and antimicrobials used in the process. LAB bacterial contamination in the range of $10^6$ to $10^7$ per ml can reduce ethanol yield by 1-3%. LAB bacteria are present in all incoming carbohydrate sources, and are present in all areas of the ethanol production plant. In industrial processes such as the manufacture of ethanol for fuel, even with active control programs to control the proliferation of LAB bacterial, carbohydrate losses to LAB bacterial can range up to several % of the total carbohydrate input, which can make the difference between profitability and non-profitability. Further, if the lactic acid content of the mash approaches 0.8% and/or acetic acid concentration exceeds 0.05%, the ethanol producing yeast are stressed and yeast metabolism is reduced. In the manufacture of certain alcoholic beverages, the proliferation of *lactobacilli* and its byproducts can unfavorably alter the taste and value of the product.

One very effective control program involves the introduction of pristinamycin-type antimicrobial agents, and particularly virginiamycin, to the process. These pristinamycin-type antimicrobial agents, and particularly virginiamycin, are preferred because: 1) they are very effective against a number of microorganisms including LAB bacteriala at low concentrations, e.g., 0.3 to 5 ppm, 2) microorganisms do not tend to develop resistance to this type of antimicrobial agent, 3) the antimicrobial agent does not significantly hinder the yeast, and 4) the antimicrobial agent is effectively destroyed by the drying of the end "waste" product so that it is not introduced indiscriminately into the environment. Usually, the "waste" byproduct, known as "Dried Distillers Grains with Solubles" (DDGS), is sold as animal feed, going 45% to dairy, 35% to beef, 15% to swine, and 5% to poultry industries. This is an important factor in the profitability of an ethanol production process, and the total amount of this byproduct produced per year is on the order of 3.5 million metric tons per year. The presence of residual antimicrobial agents in this material can adversely affect the value of this byproduct, as small residual amounts of antimicrobial agents in feed will promote the development of agent-resistant microorganisms. We have tested DDGS samples from 8 major ethanol producers using virginiamycin to control microorganisms and found no detectable amount of virginiamycin in the DDGS (<1 ppm via the validated Eurofins analysis and <1 ppb via an unvalidated experimental analytical procedure).

SUMMARY OF THE INVENTION

The present invention relates to the use of delivery systems to deliver antimicrobial agents, and particularly pristinamycin-type antimicrobial agents, polyether ionophore-type antimicrobial agents, or both, most preferably pristinamycin-type antimicrobial agents, to fluid compositions in industrial processes, particularly either directly or indirectly to mashes or feed solutions used in alcohol production via fermentation, in a pre-solubilized form where such antimicrobial agents are available to control undesirable organisms such as *lactobacilli* immediately or in a short period of time. Importantly, the formulations described herein allow the plant owner to provide effective antimicrobial control in unit operations, particularly to heat exchangers, upstream of the fermentators. At least a portion of the antimicrobial agent(s) are advantageously added to fluid compositions in industrial processes in a dissolved form, for example dissolved in an organic solvent or in a mixture of solvents. Advantageously the solvent does not promote transport of the antimicrobial agents trough organic membranes, organic slime, and the like, so as to prevent accidental exposure of workers in the event of a spill.

It has been demonstrated that for antibiotics such as penicillin that pulsed addition of antibiotics is significantly superior compared to continuous addition of the same amount of antibiotic. See, e.g., Control of *Lactobacillus* contaminants in continuous fuel ethanol fermentations by constant or pulsed addition of penicillin G, Appl Microbiol Biotechnol (2003) 62:498-502 by Bayrock, Thomas, and Ingledew. This is believed to extend to other types of antimicrobial agents. We have tested pulsed dosing versus continuous dosing on *L. paracasei* and found pulse dosing lowered the microorganism count to about 30% of the value obtained with continuous dosing, where the same amount of antimicrobial agent is added in both cases. Higher concentrations of antimicrobial agents result in higher numbers of targeted microorganisms being destroyed than are destroyed at more continuous dosing at lower concentrations. Pulsed mode addition of antimicrobial agents is believed to be more effective than continuous treatment because the higher concentration (even if present for only a short time) reduces the number of targeted microorganisms sufficiently that the rebound of surviving targeted microorganisms during periods between treatments results in fewer total viable microorganisms (averaged over time) than are obtained by continuous treatment with the same quantity of antimicrobial agent.

Our previous application Ser. No. 11/806,591 filed on Jun. 1, 2007 described several pre-dissolved where aprotic solvents are used to solubilize the pristinamycin-type antimicrobial agents, polyether ionophore-type antimicrobial agents, or both. This provided several advantages—the solvents were able to solubilize very high quantities of the pristinamycin-type and especially the polyether ionophore-type antimicrobial agents. Further, the solvents facilitated penetration of the antimicrobial agents through biofilms. This allows these agents to attack established biofilms which would otherwise be extremely resistant to intermittent treatment regimes.

However, the highly-loaded aprotic solvent/anti-microbial concentrates had problems. The ability of the solvents to facilitate carrying the antimicrobial agents through biofilms can also be problematical, as additional precautions might be necessary to prevent worker exposure to the solubilized concentrates. Additionally, many solvents had appreciable vapor pressure, which can also be a concern in a work environment. Additionally, we found that when dosing with most solvents having large amounts (i.e., more than 10% by weight) of dissolved VM, the VM would immediately precipitate on adding the concentrate to mash.

Additionally, we found appreciable degradation of certain parts of virginiamycin after solubilization, particularly the M1 factor. We have found that substantial amounts of the antimicrobial agent, including particularly virginiamycin M1, were lost both during the solubilization process and during storage. Losses on a % basis generally followed solubility—the more soluble the antimicrobial agent (i.e., virginiamycin) is in a solvent, the more antimicrobial agent lost during formulation and during storage. One exception to this was ethyl lactate. Losses were particularly evident with ethyl lactate—as much as 12% of virginiamycin M1 is lost within the first hour of formulating the solubilized virginiamycin, despite a solubility near 7.5 weight %.

Finally, to be commercially successful, the concentrates must have at least 6%, preferably at least 75, of dissolved antimicrobial agent, and the solvating materials in the antimicrobial concentrates must be Generally Recognized As Safe ("GRAS"). So while treatments of facilities with pristinamycin-type and especially the polyether ionophore-type antimicrobial agents dissolved in aprotic solvents, and particularly the solvents described in our previously filed applications, is beneficial when biofilms have built up, for normal use a less aggressive formulation may be desired, while still providing the advantages of fast delivery of agent and better dispersion in poorly mixed tanks.

Therefore, what is needed was a solubilized formulation of pristinamycin-type and/or polyether ionophore-type antimicrobial agents which could be quickly and readily dispersed in poorly mixed mash tanks.

The invention includes formulations containing greater than 1%, preferably 2% or greater by weight, for example between about 4% to about 10% by weight or between 3% and 8% by weight, of pristinamycin-type and/or polyether ionophore-type antimicrobial agents, preferably polyether ionophore-type preferably virginiamycin ("VM"), and one or more solvating components in an amount sufficient dissolve the antimicrobial agents, wherein the solvating agents are not penetrating aprotic solvents, that is, do not promote migration of the antimicrobial agent through a biofilm, and where the solvating agents are not completely ethanol, and where less than 25%, preferably less than 20%, by weight of the antimicrobial agent is degraded after 45 days storage at ambient temperature.

We have found synergistic combinations of solvents that allow us to formulate at concentrations greater than 5% (unless specified, all concentrations and parts are by weight), 6%, and even 7.5% or more, while not having antimicrobial agent inactivation issues, wherein the concentrate when added to mash under normal shear is dispersed throughout the mash and does not immediately precipitate. Most preferably the solvating agent comprises or consists essentially of one or more of an (mono-, di-, or tri-) $C_1$-$C_4$ alkyl citric acid ester, or a glycol such as propylene glycol, ethylene glycol, or dipropylene glycol. Alternatively the solvating agent can additionally comprise one or more of a carboxylic acid having more than one polar group thereon, e.g., ethyl lactate, dicarboxylic acids such as succinic acid, glutaric acid, adipic, or the like, or $C_1$-$C_4$ esters thereof, in addition to the aforesaid solvating agents. Alkyl lactates, e.g., where the alkyl group is a $C_1$-$C_4$ alkyl group, are preferred, but certain of these solvents can degrade solubilized antimicrobial agents over long-term storage.

More preferably the carboxylic acid having more than one polar group thereon is a $C_1$-$C_4$ hydroxycarboxylic acid ester or a $C_1$-$C_4$ alkyl di- or tri-carboxylic acid ester. In another alternative the solvating agents can include any of the above agents admixed with ethanol. However, certain of the glycols and the alcohol have a flash point lower than 100° C., and formulations containing these components are less preferred. Preferably the flash point (closed cup) of the solvent mixture is above 100° C., preferably above 110° C., more preferably above 120° C. These formulations provide the benefits provided of predissolved poorly-soluble antimicrobials, such as VM, added to poorly mixed fermentators. The beneficial effect, compared to similar dosages with powder, is greatest in the 6 to 24 hour time frame following the addition of the antimicrobial agent. The beneficial effect, again compared to similar dosages with powder, decreases substantially by 36 hours after dosing, and is indistinguishable from powdered VM at 48 hours after dosing, as would be expected as even in a poorly mixed fermentator. VM powder will eventually dissolve. The early effect is very beneficial, as in steady state processes if the antimicrobial agent leaves the fermentator prior to becoming dissolved, the agent may be destroyed or inactivated in downstream processes. That is, 5% w/v VM in equal volumes of a citric acid ester such as a Citroflex™ product and dipropylene glycol provided the best performance, followed by 5% w/v VM in equal volumes of Citroflex™ and Ethanol. The 6% w/v VM in equal volumes of Citroflex™ and dipropylene glycol performed less well, suggesting the VM was not fully solubilized at 6% w/v when these solvents are used.

Citroflex 2™ (triethyl citrate) is of particular interest due to its low volatility, low pour point −45 F and approval as a direct food grade additive. There appears to be a synergistic effect between Citroflex 2 when combined with DPG and ethanol separately. 1:1, 2:1, and 3:1 ratios of Citroflex 2: ethanol produce stable 5% solutions of VM. A 1:1 ratio of Citroflex 2:DPG produces a stable 6% concentrate. Increasing the ratio of Citroflex to DPG reduced the solubility of VM in those formulations.

Citric acid esters include tri-alkyl citric acid esters such as are sold under the trade name Citroflex™ (available from Morflex Inc.). Di-alkyl citric acid esters are equally useful, as are derivatives such as acetyl di- or tri-alkyl citrate. Tri-ethyl citrate, available commercially as Citroflex™ 2, is a particularly good co-solvent. Exemplary citric acid esters include triethyl citrate, tributyl citrate, and acetyl tri-n-butyl citrate. Citric acid esters are not classified as volatile organic compounds nor as hazardous air pollutants, and they combine powerful solvency with low toxicity, high flash points, and rapid biodegradability. Triethyl citrate, CAS Registry Number 77-93-0, is odorless, has a Flash Point (C.O.C.) of 155° C. (making vapors non-flammable under normal plant conditions), and has a solubility at 25° C. of 55 g per liter in water. Dipropylene glycol has a flash point of 121° C. Ethylene glycol has a flash point of 111° C., while propylene glycol has a flash point of about 99° C.

In one embodiment the material of the invention can be sold in a partially solubilized form, for example the formulation resulting from admixing 10 to 60 parts antimicrobial agent per 90 to 40 parts solvating agent, based on 100 parts total. An exemplary composition can further include 0.1 to 10 parts of surfactants and/or dispersants, and between 0.001 to 0.1 parts fungicide, such as sodium o-phenylphenate.

This novel method of adding pristinamycin-type antimicrobial agents, polyether ionophore-type antimicrobial agents, or both, to fluid compositions in industrial processes allows for new uses, including: 1) new dosing regimens for large tanks such as fermentators where such agents are traditionally added; 2) quick (under six hours) eradication of viable *lactobacilli;* 3) eradication of established biomasses containing undesired microorganisms, and for controlled pulse treatments of limited areas of a plant including for example heat exchangers. Additionally, additions of quickly available biocidal agents provide desired activity even in poorly stirred reaction vessels where traditional powdered biocidal agents are substantially ineffective.

The processes and materials of this invention are particularly useful to introduce antimicrobial agents having very low solubility in water, e.g., a solubility of less than about $10^{-2}$ and often less than about $10^{-3}$ grams per liter in water. The solubility of monensin, virginiamycin, and similar pristinamycin-type antimicrobial agents and polyether ionophore-type antimicrobial agents in water is very low. Pristinamycin-type antimicrobial agents, especially virginiamycin, have extremely low solubility in water (e.g., 0.0001 grams/l), and additionally the kinetics of dissolution are very poor. Similarly, polyether ionophores have extremely low solubility in water.

The typical treatment of ethanol plants with pristinamycin-type antimicrobial agents or polyether ionophores is provided by intermittently adding powders either as loose material or encased in dissolvable bags or packets containing a predetermined amount of the antimicrobial agent to one or more of the large mixed tanks. Two commercial prior art formulations used in ethanol treatment plants of virginiamycin comprised powder of average diameter of 5.2 to 10 microns and about 1000 microns, respectively. We have found that an impeding factor in controlling pests such as *lactobacilli* is the rate of dissolution of small granular pristinamycin-type antimicrobial agents and polyether ionophore-type antimicrobial agents in water or mash. A 0.1 gram sample of a 5.2 to 10 micron average particle size virginiamycin was placed in a beaker with 4 liters of water, and the composition was continuously and vigorously stirred. It took on the order of an hour before only a few crystals of the material remained visible. Such slow dissolution will reduce effectiveness of pulse treatments as it takes a long time for the added agents to become solubilized and effective, and will reduce the highest concentration of added agents resulting from a pulsed addition in continuous processes as some of the agent may be removed from the fermentator or other tank before the maximum amount of added agent is solubilized, and because some added agent may not dissolve at all.

In these large mixed tanks, there is often sufficient residence time and mixing for some portion of the virginiamycin to dissolve. However, mash vats and other large tanks in ethanol production plants typically are not rigorously and completely stirred, as the energy needed for such mixing can outweigh small gains in the yeast efficiency. In a poorly mixed environment, we have determine dissolution rates can take many hours, and some fraction of a granular pristinamycin-type antimicrobial agent and/or polyether ionophore-type antimicrobial agent product may never be solubilized and thereby activated. Even introduction of virginiamycin in powdered form into vigorously stirred mixing tanks containing alcoholic mash does not result in complete dissolution of the antimicrobial agent, and solid antimicrobial agent material that does not dissolve is wasted.

The invention can be broadly described as a method of controlling undesired microorganism (e.g., *lactobacilli*) metabolism in mash in an ethanol production facility, comprising adding to the mash an effective amount of one or more of a substantially water insoluble pristinamycin-type antimicrobial agent, a substantially water insoluble polyether ionophore antimicrobial agent, or both, wherein the term "substantially water insoluble" means the antimicrobial agent has a solubility in pure water at 20° C. (ambient) of about 0.1 grams per liter or less, and wherein at least a portion of the substantially water insoluble antimicrobial agent(s) is added to the mash in the form of an organic solution comprising at least one organic solvent (selected from those listed above as a solvating agent) having said substantially water insoluble antimicrobial agent(s) dissolved therein, said organic solution advantageously comprising at least 1 gram per liter, preferably at least 2 grams per liter, for example at least 10 or 50 grams per liter, of said antimicrobial agent(s).

In one embodiment the substantially water insoluble antimicrobial agent comprises, consists essentially of, or consists of a substantially water insoluble pristinamycin-type antimicrobial agent. In another embodiment the substantially water insoluble antimicrobial agent comprises or consists essentially of a substantially water insoluble polyether ionophore antimicrobial agent. In one preferred embodiment the substantially water insoluble antimicrobial agent comprises or consists essentially of at least one of virginiamycin and semduramycin, and at least a portion of the antimicrobial agent(s) is added to the mash in the form of an organic liquid comprising at least of the aforesaid solvating agents having said substantially water insoluble antimicrobial agent(s) dissolved therein. In another embodiment the substantially water insoluble antimicrobial agent comprises or consists essentially of monensin and at least a portion of the monensin is added to the mash in the form of an organic liquid comprising at least one of the aforesaid solvating agents having said monensin dissolved therein. By "organic liquid" or "organic solution" we mean a liquid which preferably comprises at least 50% by weight of one or more organic solvents listed above as a solvating agent, e.g, a glycol, for example dipropylene glycol, a citric acid ester, a polyfunctional organic acid, preferably ethyl lactate, ethanol, mixtures thereof.

In a preferred embodiment the substantially water insoluble antimicrobial agent comprises, consists essentially of, or consists of a substantially water insoluble pristinamycin-type antimicrobial agent, and at least a portion of said pristinamycin-type antimicrobial agent is added to the mash in the form of an organic solvent-containing liquid comprising more than 10 grams per liter, preferably more than 20 grams per liter, more preferably more than 40 grams per liter, of solubilized pristinamycin-type antimicrobial agent. In another embodiment the substantially water insoluble antimicrobial agent comprises a substantially water insoluble pristinamycin-type antimicrobial agent, and at least a portion of said pristinamycin-type antimicrobial agent is added to the mash in the form of an organic solvent-containing liquid comprising at least one of the aforesaid solvating agents, said organic liquid comprising more than 10 grams per liter, preferably at least 20 grams per liter, more preferably more than 40 grams per liter, of pre-solubilized pristinamycin-type antimicrobial agent. In another embodiment the substantially water insoluble antimicrobial agent comprises, consists essentially of, or consists of a substantially water insoluble pristinamycin-type antimicrobial agent which is added to an aqueous solution or mash in the form of an organic liquid, wherein the organic liquid preferably comprises at least one of the aforesaid solvating agents, said organic liquid comprising more than 10 grams per liter, preferably at least 20 grams per liter, more preferably more than 40 grams per liter, of said pristinamycin-type antimicrobial agent.

In another preferred embodiment the substantially water insoluble antimicrobial agent comprises, consists essentially of, or consists of a substantially water insoluble polyether ionophore-type antimicrobial agent, and at least a portion of said antimicrobial agent is added to the mash in the form of an organic solvent-containing liquid comprising the aforesaid solvating agents and more than 10 grams per liter, preferably more than 20 grams per liter, more preferably more than 40 grams per liter, of solubilized antimicrobial agent. In another embodiment the substantially water insoluble antimicrobial agent comprises, consists essentially of, or consists of a substantially water insoluble polyether ionophore-type antimicrobial agent, and at least a portion of said antimicrobial agent is added to the mash in the form of an organic solvent-containing liquid comprising or consisting essentially of one or more of the aforesaid solvating agents, said organic liquid comprising more than 10 grams per liter, preferably at least 20 grams per liter, more preferably more than 40 grams per liter, of pre-solubilized antimicrobial agent. In any embodiment the addition of small amounts of surfactants and dispersants is included, as these agents can help dispersion without affecting the basic improvement made by the invention. In another embodiment the substantially water insoluble antimicrobial agent comprises, consists essentially of, or consists of a substantially water insoluble polyether ionophore-type antimicrobial agent which is added to an aqueous solution or mash in the form of an organic liquid, wherein the organic liquid comprising or consisting essentially of one or more of the aforesaid solvating agents, said organic liquid comprising more than 10 grams per liter, preferably at least 20 grams per liter, more preferably more than 40 grams per liter, of said antimicrobial agent.

In another embodiment the substantially water insoluble antimicrobial agent comprises, consists essentially of, or consists of a substantially water insoluble polyether ionophore antimicrobial agent, and at least a portion of said antimicrobial agent is added to the mash in the form of an liquid comprising one or more of at least one of, or consisting essentially of, one or more of the aforesaid solvating agents, at least one alkyl acetate, at least one alkyl lactate, ethanol, or combination thereof, said organic liquid comprising more than 2 gram per liter, preferably more than 10 grams per liter, more preferably more than 20 grams per liter, for example at least 40 grams per liter of said antimicrobial agent. In another embodiment at least a portion of said antimicrobial agent is added to the mash in the form of an organic liquid comprising or consisting essentially of one or more of the aforesaid solvating agents, at least one alkyl acetate, at least one alkyl lactate, or combination thereof, said organic liquid comprising more than 2 gram per liter, preferably more than 10 grams per liter, more preferably more than 20 grams per liter, for example at least 40 grams per liter of said antimicrobial agent. In any embodiment above, having between 1% and 50%, preferably between 3% and 30%, for example between 5% and 25% by weight of triethyl citrate (Citroflex 2) is highly advantageous.

We have found surprising synergy in solubility of certain solvents. The solubility of virginiamycin in triethyl citrate is quite low, between 2.5% and 5% by weight based on the weight of solution. The solubility of virginiamycin in commercial denatured ethanol is less than about 2.5% by weight based on the weight of solution. But with any of a 3:1, 2:1, or 1:1 parts by weight ethanol to triethyl citrate, formulations containing over 5% by weight virginiamycin were readily prepared. Similarly, we found the solubility of virginiamycin in ethyl lactate was about 7.8% by weight, but fonnulations of 3:1 and 2:1 parts ethyl lactate to triethyl citrate, and formulations of 1:1:1 and 1:1:0.5 parts ethyl lactate to ethanol to triethyl citrate were all readily prepared which contained 7.5% by weight virginiamycin. Further, in the mixed solvent formulations described here the degradation of virginiamycin over time was much reduced compared to the degradation in ethyl lactate alone.

Use of ethanol as a co-solvent is preferred for commercial products even though the resultant flash point of the mixture is below 104° F.

In another embodiment at least a portion of said antimicrobial agent is added to the mash in the form of an organic liquid comprising at least 70% by weight of ethanol in water. Water-free ethanol is preferred for increased antimicrobial agent stability during storage of the solvated formulations.

In another embodiment at least a portion of said antimicrobial agent is added to the mash as a composition comprising particles comprising said substantially water insoluble antimicrobial agent(s), said composition being in the form of a slurry comprising particles and any of the organic liquids or liquids comprising the antimicrobial agents that were described in the many embodiments above.

In another embodiment the ethanol production facility comprises a tank having an inlet and an outlet and a heat exchanger having an inlet and an outlet and being flowingly connected to the outlet of said tank so mash flows from the tank to the heat exchanger, the method comprising adding to the mash at a point between the tank outlet and the outlet of the heat exchanger an effective amount of said substantially water insoluble antimicrobial agent in the form of an organic liquid comprising at least one organic solvent having said substantially water insoluble antimicrobial agent(s) dissolved therein, said organic liquid comprising more than 2 gram per liter, preferably more than 10 grams per liter of said antimicrobial agent(s).

In another embodiment at the ethanol production facility comprises at least one heat exchanger, said method comprising adding at least a portion of said antimicrobial agent to said mash passing through said heat exchanger. In another embodiment the ethanol production facility comprises at least one mixed tank and at least one heat exchanger, the method comprising:
  a) adding to the mash in said tank a portion of the substantially water insoluble antimicrobial agent(s); and
  b) adding to the mash passing through said heat exchanger a portion of the substantially water insoluble antimicrobial agent(s) in the form of an organic liquid comprising at least one organic solvent having said substantially water insoluble antimicrobial agent(s) dissolved therein, said organic liquid comprising more than 2 grams per liter of said antimicrobial agent(s).

In another embodiment at least a portion of said antimicrobial agent is added to the aqueous composition such as the mash by a metering pump which pumps a liquid composition comprising said antimicrobial agent into said mash.

The formulations discussed above are useful for a variety of applications in addition to controlling undesired microorganisms in ethanol production facilities. Antimicrobial agents such as virginiamycin are used in a large number of applications, including the above-mentioned use as a supplement given to animals to encourage growth. The compositions of this invention are active in mash vats and other large tanks in ethanol production plants that are not rigorously and completely stirred, where powdered agents are substantially ineffective. Liquid compositions of this invention can also be sprayed onto surfaces of the process equipment which are only intermittently wetted by for example mash, for example in upper parts and tops of tanks and fermentors, where the liquid can dry and leave a small but antimicrobially effective amount of antimicrobial agents which will discourage formation of undesired biomass resulting from occasional and often accidental wetting by mash or other nutrient-rich liquid. In a poorly mixed environment, dissolution of added powders can take many hours, and some fraction of a granular pristinamycin-type antimicrobial agent and/or polyether ionophore-type antimicrobial agent product may never be solubilized and thereby activated. The solutions and slurries of various embodiments of this invention (using appropriate solvents) are equally applicable to use in those fields of use, providing a number of benefits including reduced dust, easy incorporation of antimicrobial agents into feed, and greater stability and dispersability in water systems.

One aspect of this invention is to supply a single-phase liquid comprising one or more of dissolved antimicrobial agents, particularly pristinamycin-type antimicrobial agents, polyether ionophore-type antimicrobial agents, or both, to mash or to an ingredient forming the mash in an ethanol production plant, where the pre-dissolved pristinamycin-type antimicrobial agents, polyether ionophore-type antimicrobial agents, or both are added in a continuous mode, in a pulsed mode, or in some alternative hybrid mode. The liquid comprising the dissolved antimicrobial agents advantageously comprises a single phase, as stability problems associated with emulsions are absent. The liquid containing the dissolved pristinamycin-type antimicrobial agents, polyether ionophore-type antimicrobial agents, or both comprises at least about 1 gram of antimicrobial agent per liter, for example at least 5 grams of antimicrobial agents per liter, more preferably at least 10 grams of antimicrobial agents per liter, even more preferably at least 20 grams or at least 50 grams of antimicrobial agents per liter.

Preferred solvents and solvent mixtures are those that exhibit both very low to negligible adverse impacts on yeast and on the byproduct DDGS (in the amounts necessary to solubilize and deliver the required dosage of antimicrobial agent), that are not considered volatile organics, and that solubilize more than 10 grams of virginiamycin (or other pristinamycin-type antimicrobial agents, polyether ionophore-type antimicrobial agents, or both) per liter, preferably more than 20 grams per liter, more preferably at least 50 grams of virginiamycin (or other pristinamycin-type antimicrobial agents, polyether ionophore-type antimicrobial agents, or both) per liter.

Dipolar aprotic solvents disclosed in our earlier applications for patent may not be useful in for example plants that manufacture ethanol-containing products for human consumption. Dipolar aprotic solvents disclosed in our earlier applications for patent also may not be useful for routine use in for example plants where accidental worker exposure is a concern. Technical grade of solvents is often preferred if the ethanol is being used for fuel, as high purity is often not required, and the solvents will metabolized or recovered in the ethanol/gasoline formulation. For ethanol as a beverage, advantageously the solvent is added in a more pure form, and the solvent is a material naturally found in the beverage product, or the solvent is most preferably consumed by yeast or otherwise treated so as not to enter the beverage. In plants producing ethanol for human consumption, the preferred solvents are those that solubilize more than 2 gram, and preferably more than 20 grams, of antimicrobial agent per liter, and are consumed by yeast, are naturally present in the beverage, have low toxicity, and/or are eliminated from the beverage by further processing. Generally Regarded As Safe compounds are commercially required. For this reason, certain glycols (propylene glycol, dipropylene glycol, etc) are not preferred in some formulations, though the solvents perform well with respect to the physical aspects of the formulations, e.g., solubility, stability, dispersability, and the like. A useful polar organic solvent is ethanol, where a reasonably high concentration (~70 g/l) of pristinamycin-type antimicrobial agents (e.g. virginiamycin) and somewhat similar amounts of polyether ionophore-type antimicrobial agents can be dissolved if the liquid is at least 75% by weight ethanol. A problem with pre-solubilized liquid compositions is the presence of highly flammable mixtures—ethanol has a flash point of about 55° F.

Certain $C_1$ to $C_5$, preferably $C_1$ to $C_4$ alkyl esters of low molecular weight ($C_1$ to $C_4$, preferably $C_2$ to $C_3$) organic acids, particularly alkyl acetates, propionates, butyrates, lactates, and the like are also known to be benign in terms of yeast and human exposure, and the preferred antimicrobial agents of this invention all exhibit significant solubility in these solvents. Therefore, advantageously the alkyl moiety in the alkyl acetates, alkyl lactates, and the like is advantageously $C_1$ to $C_4$, and is preferably is ethyl. Exemplary solvents include ethyl lactate, ethyl acetate, ethyl 2-hydroxyacetate, and the like. Inclusion of hydroxyl groups onto the alkyl moiety or acid moiety are useful.

So-called "green" solvents, which have little effect on humans in reasonable concentrations, are preferred. Such solvents typically have LD50 concentrations (for rats, rabbits, and other test animals) of at least 5 grams per kilogram. A preferred solvent is ethyl lactate, $CH_3CH(OH)CO_2C_2H_5$ which we have found can dissolve about 92 grams of virginiamycin per liter. Ethyl acetate (ethyl ethanoate), used for decaffeinating coffee and for flavorings, is also a very useful benign solvent exhibiting good solubility of the antimicrobial agents used in this invention. Amyl acetate, while fairly benign, has a useful solubilizing effect for monensin but the solubility of virginiamycin in this solvent is at the lower end of what is commercially feasible.

Preferred solvating agents are citric acid esters having $C_1$ to $C_4$, preferably $C_2$ to $C_3$, alkyl groups attached thereto. Trimethyl citrate (CAS No. 1587-20-8) is a solid at room temperature and has a high flash point. Triethyl citrate is a liquid at room temperature and has a flash point near 150° C. This compound is used in food industries, and is especially useful when the fermentation process results in alcohol for human consumption. Tripropyl citrate (CAS No. 1587-21-9) is useful, as is acetyl triethyl citrate (CAS 77-89-4). Similar combinations of acetylated trimethyl citrate and tripropyl citrate are useful.

Advantageously, the flammability of the solvent is such that the compositions of this invention can be used in an ethanol-producing plant without special labeling and handling. There are stringent rules relating to the presence of flammable solvents in additives and chemicals stored in ethanol production plants. For example, use of 90% ethanol in upstream processes is tightly restricted, despite the product of the plant being for example 90% ethanol. Generally material with a flash point of 200° F. or above is often considered to be non-combustible, though the federal, state, and local regulations relating to ethanol production facilities may have different definitions of flammable and restricted solvents. A preferred composition has a flash point of about 201° F. or higher, more preferably 110° C. or higher, and be considered non-combustible while solubilizing 10 to 100 grams virginiamycin per liter.

As used herein, when we discuss monensin we are talking about either Monensin type A alone, monensin comprising a majority of type A and one or more of types B, C, and D, and "monensin sodium." As used herein, when we discuss virginiamycin we are talking about a formulation containing virginiamycin type A, virginiamycin type B, or very preferably a combination of the two.

Advantageously, the solvents must have a sufficiently high concentration of antimicrobial agent and must not (at the anticipated concentrations of the solvent in the fermentors) adversely affect yeast. Typically, sufficient control of *lactobacilli* is obtained in the tanks, fermentors, and the like with between 0.2 ppm to 1 ppm, and typically about 0.4 ppm to 0.5 ppm antimicrobial agent, preferably virginiamycin (though occasionally a spike of up to 3 or 4 ppm or so may be necessary under some conditions). Treatment with polyether ionophores usually requires between 0.3 ppm to 3 ppm, and typically between 0.5 ppm and 2 ppm polyether ionophore. Further, plants are sized that for most applications a "dose" of virginiamycin sufficient to treat a large mixed tank is between one ounce and one pound of active ingredient. Assuming a formulation density of 1 g/cc, a liquid having 50 grams per liter of dissolved antimicrobial agent, e.g., virginiamycin, an operator will need to add 10 parts of solvated antimicrobial agent per million parts of liquid into the mash to provide the desired 0.5 ppm concentration of antimicrobial agent. Further, the normal dosage of 1 ounce to one pound for dosing of large mixed tanks in industrial settings would require between about 0.6 to 9 liters of solvated antimicrobial agent, which is an easy volume to ship, store, and handle since the material has no dangerous flash point. If the solubilized pristinamycin-type antimicrobial agents, polyether ionophore-type antimicrobial agents, or both are only used for spotted pulse treatments of selected equipment, for example heat exchangers, the amount of solvating compounds in the mash will more likely be well below a few ppm, and the yeast will consume the solvating agents. To be useful, these solvents used to formulate the liquid having 1 gram dissolved antimicrobial agent per liter should not adversely affect yeast at concentrations of up to about 500 ppm.

Generally, a liquid having only 1 gram antimicrobial agent dissolved therein per liter of liquid may not be economically practicable for use in dosing large tanks. Such a liquid can still be economically and feasibly used, however, for intermittent pulsed treatment of small volumes of mash, for example the volume of mash passing through a heat exchanger for some predetermined duration of a dose to treat the heat exchanger.

For solubilized virginiamycin embodiments of this invention, it may be useful to have a portion or all of the virginiamycin be in a modified form, such as acetylated, to increase solubility characteristics in water without effectively destroying the utility of the antimicrobial agent. Typically, disclosures herein center on virginiamycin, as that is the preferred antimicrobial agent. It should be appreciated, however, that these disclosures are also generally applicable to other pristinamycin-type antimicrobial agents and polyether ionophore-type antimicrobial agents.

For plants producing ethanol for use as fuel, other useful organic solvents are those that in the concentrations added are not detrimental to yeast, and which are separated from the aqueous mash in the distillation process so as to follow the ethanol, where said solvent is of the type capable of being blended into gasoline with no adverse effects. Advantageously, in some embodiments of the invention, the medium comprising the pristinamycin-type antimicrobial agents, polyether ionophore antimicrobial agents, or both does not require special permitting and handling in an ethanol plant.

Another aspect of this invention is to supply a multi-phase liquid comprising one or more of dissolved antimicrobial agents, particularly pristinamycin-type antimicrobial agents, polyether ionophore-type antimicrobial agents, or both, to mash or to an ingredient forming the mash in an ethanol production plant, where the pre-dissolved pristinamycin-type antimicrobial agents, polyether ionophore-type antimicrobial agents, or both are added in a continuous mode, in a pulsed mode, or in some alternative or hybrid mode.

In one embodiment the material containing the dissolved pristinamycin-type antimicrobial agents, polyether ionophore-type antimicrobial agents, or both can be supplied as a solid that melts at mash temperature, or as a liquid.

We have found that prior art formulations do not provide the anticipated concentration profile when admixed into tanks, as it takes a long period of time for such particles to dissolve in aqueous mash, and the hydrodynamic conditions and residence time of the particles in the mixing tank are such that some of the antimicrobial material will not dissolve but will be effectively wasted. Therefore, a pulse treatment of a mixed tank in fact does not provide an active concentration of material as is often depicted in literature, that is, reaching a peak which subsequently declines as the pulse or dose is diluted by untreated incoming mash. Rather, the concentration of effective antimicrobial agents in a dosed mixed tank using prior art treatments tends to climb slowly and peaks at a point where a significant amount of the material has already left the mixed tank, and the peak concentration and the area under a concentration-time curve will both be much lower than anticipated. Using compositions of this invention, the effective dose (that is, the dose of antimicrobial agent that is effectively used to control targeted microorganisms) more nearly matches the theoretical dose. Second, higher effective concentrations (and therefore increased efficacy) of biocide are achieved from a pulse dose of the composition of this invention than is obtainable with the same mass of slow dissolving particles. Third, tailoring a pulse in terms of effective concentration versus time and the duration of a pulse can be achieved. Fourth, the compositions of this invention can be utilized to pulse treat unit operations such as heat exchangers and small mixed tanks (especially for example saccharization tanks) where treatment with prior art formulations was not practical or possible because much of the added product would be flushed from the targeted unit operations prior to dissolution. Finally, fifth, using prior art formulations only the solubilized portion of antimicrobial agents were effective. The targeted bacteria have an effective diameter of about a micron. If the antimicrobial agent precipitates from the organic liquid when the liquid is added to the mash, the precipitate will be of a size near that of a bacteria, say between ~0.02 microns to ~2 microns, and a measure of control is obtainable from direct solid antimicrobial agent to microorganism contact and/or interaction, thereby increasing the efficacy of a mixture of soluble and precipitated particulate biocide of the current invention as compared to the efficacy of a mixture of soluble and particulate biocide of the prior art formulations.

It is recognized that in some cases adding solubilized antimicrobial agents to mash or an excess of aqueous liquid will result in substantially instantaneously formed submicron to nanometer sized particles in a "slurry", where the formation of particles and the resultant size of particles depends in large measure on the hydrodynamic conditions at the point the solubilized antimicrobial agents are added to the mash. Precipitating submicron particles of antimicrobial agent which in some cases might occur on mixing an organic liquid containing the agents with water or mash is more advantageous that trying to provide powdered submicron antimicrobial agents. The most significant drawback of powdered submicron antimicrobial agents is the possibility of dust, both from normal operations and from normal shipping and handling of product. Submicron particles can act much like smoke or dust in the air. The compositions of this invention reduce antimicrobial agent duct to negligible levels.

It may be useful if flow conditions are not sufficiently turbulent to add the solubilized and/or particulate antimicrobial agents to a small sidestream under high shear, where this sidestream can then be reintroduced to the mash. This mixing can be done immediately before introducing the antimicrobial agent to the mash, and can utilize high shear, or an elevated temperature, or any combination of the above as needed depending on the composition of the material containing the antimicrobial agents.

We have mentioned continuous treatment, pulsed treatment, and hybrid treatments. A pulsed treatment supplies a single dose of antimicrobial agent to a receiving vessel, usually a mixed tank, at regular intervals that are advantageously spaced such that the concentration of the antimicrobial agent reaches a high soon after adding the dose and then declines as the material degrades or is transported out of the tank, which will occur for example in continuous production plants. We have actually found that there is a significant period of time between adding a dose of prior art formulations and the time of the measured peak of active (dissolved) antimicrobial agent. We have further found that the actual peak of dissolved antimicrobial agent is not only more delayed from the theoretical peak but is also at a significantly lower concentration value than the theoretical concentration (assuming instantaneous delivery, mixing, and dissolution). That is, adding a 2 ppm dose of antimicrobial agent of the type used in the prior art may give a peak of for example 1.5 ppm (or even less) of dissolved antimicrobial agent in the mash, where the main cause is undissolved antimicrobial particles and agent carried from the mixing tank prior to dissolution. Using formulations of the current invention allow active concentrations to be much closer to the theoretical concentrations. Further, the amount of antimicrobial agent in a pulse can be introduced over time, allowing the operator to extend the peak concentration for an operator-definable period of time to maximize effectiveness. This is one hybrid method of introducing one or more pristinamycin-type antimicrobial agents, polyether ionophore-type antimicrobial agents, or both to mash that was not possible using prior art formulations.

Another aspect of this invention is to supply pulsed treatments of either or both of 1) the above-described liquid comprising pre-dissolved pristinamycin-type antimicrobial agents, pre-dissolved polyether ionophores, or both, to locations upstream of a particular targeted unit operation, for example a heat exchanger or a saccharization tank in an ethanol production plant, where the pulse is not diluted by passing through a large mixed tank or the like prior to reaching the heat exchanger or saccharization tank. Of course, these unit operations can also be treated in continuous mode using the compositions of this invention, but many benefits of this invention will not be realized by continuous treatments. Adding a pulsed dose of antimicrobial agent, where the pulse is added in an amount sufficient to provide the desired concentration of active antimicrobial agent for the desired period of time, can greatly reduce heat exchanger fouling. It is extremely desirable to be able to "dose" a small volume of the mash passing through heat exchangers on a more frequent interval than is needed to treat the bulk of the product. Heat exchangers provide a very attractive location for microorganisms to proliferate, as the temperature is by the nature of heat exchangers moderated from extremes found in tanks, and further there is a continuous flow of nutrients. Heat exchangers become fouled by microorganism growth, especially *lactobacilli*, and the growth forms a film that significantly reduces the efficiency of the heat exchangers. Treatment of only very small volumes of mash (that mash passing through the heat exchanger during the duration of the pulse) are needed, so the overall loading of antimicrobial agents to the total volume of mash is minimized.

Pulse treatment of heat exchangers with pre-dissolved antimicrobial agents of this invention will typically add a negligible amount of solvent to the mash volume. More stringent control of *lactobacilli* and/or other microorganisms is desired in heat exchangers. Such treatments can replace intermittent or continuous treatments added to large tanks but preferably supplement intermittent or continuous treatments added to large tanks. If the treatment of such heat exchangers is in addition to pulsed treatment of mixed tanks upstream of the heat exchangers, then advantageously at least some of the pulsed doses of antimicrobial agent directed only to the heat exchanger should be timed to coincide with the times of maximum concentration of active antimicrobial agent in the mash entering the pipes leading to the heat exchanger. Generally, the absolute amount of pristinamycin-type antimicrobial agents, polyether ionophores, or both added in a pulsed treatment of a heat exchanger is a small fraction of the amount of pristinamycin-type antimicrobial agents, polyether ionophores, or both added to large mixed tanks. A program of pulse treatment of a heat exchanger may result in treating only 1-5% of the mash, and this 1-5% is typically diluted by a factor of 20 to 100 when the pulse reaches the next large mixing vessel. Use of solubilized antimicrobial agents to treat specific unit operations that have a low residence time will add a negligible amount of solvent to the mash.

Additionally, the concentration of pristinamycin-type antimicrobial agents, polyether ionophores, or both in the pulsed treatment can be very high, above 3 ppm, for example 4 or more ppm, where once the pulse reaches a large mixed tank the increase in antimicrobial agent concentration in the large mixed tank is instantly diluted to perhaps 0.3 to 0.5 ppm, which is a useful treatment dose for most large vessels. Without pre-dissolving the antimicrobials, there is no method to treat small units such as heat exchangers effectively with high dose concentrations, as added powder will not dissolve until well after mash has passed through the small unit.

For any production system, optimizing the pulse concentration, duration, and frequency is within the capabilities of one of ordinary skill in the art. Many benefits of this invention (faster active ingredient delivery) can be achieved by merely pre-wetting a prior art powdered pristinamycin-type antimicrobial agents or polyether ionophores in a solubilizing solvent such that the solvent wets the powder and begins the dissolution process even as the powder is being added to the process, e.g., to the mash tanks. Alternatively, pristinamycin-type antimicrobial agents or polyether ionophores can be solubilized in solvent, and then admixed with water to form an emulsion or an aqueous composition with the solvent(s), and active pristinamycin-type antimicrobial agents or active polyether ionophores therein, and the emulsion or aqueous composition can be admixed with the material to be treated, e.g., mash.

The use of this invention has a clear advantage of allowing automated control and dispensing of antimicrobial agents, thereby minimizing operator time, operator exposure, and potential errors associated with having the treatment be done manually.

Another aspect of this invention is to simultaneously add dissolved and slurried antimicrobial agents simultaneously or nearly simultaneously to mash. This pre-dissolved agent gives the injected fluid or slurry a small but almost instantaneous effect. The particles can provide the bulk of the antimicrobial agents over most of the duration of a pulsed dose. Such a mixture should be made intermediately before adding it to the mash, as the solvent (if saturated with antimicrobial agents) will eventually over extended periods of time result in particle growth of particles in the slurry.

In each of the above-described embodiments the antimicrobial agent may comprise, consists essentially of, or consists of a pristinamycin-type antimicrobial agent. The term "pristinamycin-type antimicrobial agent" encompasses but is not limited to doricin, patricin, vernamycin, etamycin, geminimycin, synergistin, mikamycin, ostreogrycin, plauracin, streptogramin, pristinamycin, pyostacin, streptogramin, vernamycin, virginiamycin, viridogrisein, maduramycin, plauracin, and griseoviridin. However, the preferred antimicrobial agent of this type is virginiamycin, available for example from Phibro Animal Health Corp of Ridgefield Park, N.J. In each of the above-described embodiments the antimicrobial agent may comprise, consists essentially of, or consists of a polyether ionophore antimicrobial agent, a number of which are known in the art, and include for example lasalocid, maduramycin, monensin, narasin, salynomycin, and semduramycin, but the preferred polyether ionophore antimicrobial agents are monensin and semduramycin. The pristinamycin-type antimicrobial agent and polyether ionophore antimicrobial agents can be used in the various embodiments of this invention alone, together, or in combination with other antimicrobial agents including bactricin, penicillin, tetracycline, oxytetracycline, and the like.

While the invention is primarily useful for substantially water-insoluble pristinamycin-type antimicrobial agents and polyether ionophore antimicrobial agents, this invention is also useful for other antimicrobial agents and for blends. A variety of vendors market blends of antibiotics for treatment of microorganisms. Most blends include a number of agents and include agents to which microorganisms readily become resistant. Blends of agents that are not pristinamycin-type antimicrobial agents and/or polyether ionophore antimicrobial agents are not particularly preferred, as even if a blend comprises a pristinamycin-type antimicrobial agent or polyether ionophore antimicrobial agent, the amount of this agent is generally present in low amounts, increasing the risk of developing a resistant microorganism. Nevertheless, such blends can be readily accommodated by the methods and materials of this invention.

In one aspect of the invention the solvating agent may additionally include an alkyl or di-alkyl sulfoxide.

The preferred antimicrobial agents consist of, or consist essentially of, pristinamycin-type antimicrobial agents and/or polyether ionophore antimicrobial agents. Preferred solvating agents are biodegradable. A fungicide or other biocides may be present in a small amount to provide a composition that has an extended shelf life.

The preferred dose, of used alone, is at least 0.25 ppm and preferably at least 0.3 ppm of pristinamycin-type antimicrobial agents or 0.4 ppm and preferably 0.5 ppm of polyether ionophore antimicrobial agents. A mixture of antimicrobial agents which makes sense from a scientific and economic standpoint is a mixture of pristinamycin-type antimicrobial agents and polyether ionophore antimicrobial agents. At least one of these should be added to the mash in its preferred effective dosage, but advantageously both can be added to mash at the lower ends of their preferred effective concentrations. This mixture includes only antimicrobial agents to which microorganisms rarely develop effective resistance, and the use of the two in combination provides different mechanisms of microorganism control and different efficiencies in the various environments (varying pH, sugar content, nutrients, contaminants, and the like present in the mash). Polyether ionophore antimicrobial agents are more readily solubilized by organic solvents, and therefore are more readily used when solubilized antimicrobial agents are desired. However, virginiamycin is the preferred antimicrobial agent, and its use in tanks is greatly preferred. If the solubilized antimicrobial agents are used only to treat limited operations, such as heat exchangers, the resulting mash in downstream mixed tanks in the production system may have a trace but not an effective amount of this agent. Solubilized antimicrobial agents added to treat small unit operations such as heat exchangers, and which add a very small amount of antimicrobial agent when viewed over the entire volume of mash in subsequent mixed tanks and fermentors, are beneficially of the same type of antimicrobial agent as are used to treat tanks.

The invention is intended to be illustrated by, but not limited to, the Examples described here.

EXAMPLE 1

The solubility of monensin, virginiamycin, and similar pristinamycin-type antimicrobial agents and polyether ionophore-type antimicrobial agents in water is very low. Much more important, however, is the rate of dissolution of small granular pristinamycin-type antimicrobial agents and polyether ionophore-type antimicrobial agents in water. A 0.1 gram sample of a 5.2 to 10 micron average particle size virginiamycin was placed in a beaker with 4 liters of water, and the composition was continuously stirred. The presence of undissolved crystals was very evident. It took, on the order of an hour before only a few crystals of the material remained visible.

The solubility of virginiamycin in several solvents is known, and the solubility in other solvents were determined. Some of the solvents proved useful, while others could not provide a stable product. The results are presented in the Tables below.

Table 1, Virginiamycin solubility in grams per liter of solvent

| methyl soyate ester | <1 gram per liter |
| 2-ethyl hexyl lactate | ~24 grams per liter |
| ethyl lactate | ~92 grams per liter |
| 70% ethanol/30% water | ~70 grams per liter |

These literature values do not reflect our experience, where putting 80 grams per liter of virginiamycin into solution is very difficult. It may be that the literature used only certain fractions of the virginiamycin, e.g., the M1 fraction, or different activities of virginiamycin. We have found solubility of virginiamycin varies with activity of the product. In addition, literature data was obtained for the solubility of "virginiamycin-type" compounds in a variety of solvents, including methylethylketone (35 g/l), butyl acetate (35 g/l), ethyl acetate* (~205 g/l), and amylacetate (>4 g/l). Literature searches show monensin is much more soluble in a variety of solvents than is virginiamycin, and monensin is very soluble in ethyl acetate.

EXAMPLE 2

Formulation work commenced with initial screening of individual solvent systems based on their ability on their own to solubilize VM. From this initial screening, a list of potential candidates was developed which included: DMSO, ethyl lactate, ethanol, dipropylene glycol, propylene glycol, and triethyl citrate. These solvent systems were evaluated both individually and in numerous combinations to determine the maximum level of VM that could be solubilized by these solvents and solvent blends while also studying stability of the VM active ingredient in these systems.

Bench scale survey tests were performed to identify solvating agents that have reasonable solubility without having membrane-penetrating qualities. In the examples here, the solvents are reported as parts by weight based on the other solvents, and the antimicrobial agent is reported as weight %. A composition having 50 grams ethanol, 50 grams ethyl lactate, and 7.6 grams virginiamycin would be shown as a 7.5% VM in 1:1 ethanol/ethyl lactate. To screen solvents and cosolvents, a large number of examples and comparative examples were run. The following are pertinent results from a few of the tests performed.

| Test #1 Evaluate VM solubility in ethanol | | |
|---|---|---|
| A) 7.5% VM in ethanol (18.75 g of VM/250 mL) | MIX START | 11:11 AM |
| | MIX STOP | 12:16 AM |
| | RESTART | 12:22 AM |
| | STOP | 2:05 PM |
| BROWN OPAQUE LIQUID, STRATIFIED, COLD BEAKER | | |

| Test #2: 7.5% VM 250 mL ETHANOL (LAB GRADE) | | |
|---|---|---|
| | MIX START | 2:28 PM (20° C.) |
| 18.75 g OF VM | STOP | 3:00 (16° C.) |
| | START | 3:02 (18° C.) |
| | STOP | 3:38 |
| DARK BROWN OPAQUE LIQUID, STRATIFIED, COLD | | |

| Test #3: 3.75% VM 250 ETHANOL (INDUSTRIAL GRADE) | | |
|---|---|---|
| 9.38 g OF VM | START | 3:36 PM (20° C.) |
| | STOP/START | 4:05 (15° C.) |
| | START | 4:39 |
| | STOP | 5:08 |
| DARK BROWN, OPAQUE LIQUID, STRATIFIED | | |
| Test #4: 2.0% 150 mL ETHANOL (INDUSTRIAL) | | |
| 3 g OF VM | START | 9:40 AM |
| | STOP | 10:24 (21° C.) |
| | START | 10:22 |
| | STOP | 10:48 (20° C.) |
| DARK BROWN OPAQUE LIQUID, SMALL AMOUNT SEPARATION | | |
| Test #5: Evaluate 5.0% VM solubility in Ethylhexyl Salicylate (HALLBRITE OS-USP) | | |
| 7.5 g OF VM/150 mL HALLBRITE OS-USP | START | 11:00 AM (20° C.) |
| | STOP | 11:33 (25° C.) |
| | START | 11:36 |
| BROWN OPAQUE LIQUID, SOME SEPARATION (SMALL/LITE) | STOP | 12:05 (24° C.) |
| | START | 12:30 |
| | STOP | 1:30 (25° C.) |
| Test #6: Evaluate 2.5% VM solubility in HALLBRITE OS-USP | | |
| (5.0% 150 mL/7.5 g) | | |
| (5.0% 150 mL/7.5 g) → 7.5 mL ABOVE 5.0% SOLUTION | START | 1:40 |
| 7.5 mL HALLBRITE OS-USP | STOP | 2:10 |
| BROWN OPAQUE LIQUID, SOME SEPARATION | | |
| Test #7: Evaluate 5.0% VM solubility in PROPYLENE GLYCOL | | |
| | START | 2:15 PM (22° C.) |
| 7.5 g OF VM/150 mL PROPYLENE GLYCOL | STOP | 2:45 (27° C.) |
| | START | 2:49 (26° C.) |
| | STOP | 3:17 |
| CARMEL/BROWN CREAMY/OPAQUE LIQUID | | |
| Test #8: Evaluate 2.5% VM solubility in PROPYLENE GLYCOL | | |
| 75 mL 5% SOLUTION (150 mL PROPYLENE GLYCOL + 7.5 G VM) | START | 3:25 PM |
| | STOP | 4:00 PM |
| CARMEL/BROWN 'CREAMY' LIQUID | | |
| Test #9: Evaluate 5.0% VM solubility in DI PROPYLENE GLYCOL | | |
| 7.5 G OF VM/150 mL DI PROPYLENE GLYCOL | | |
| | START | 4:05 PM (22° C.) |
| | STOP | 4:37 (26° C.) |
| TRANSLUCENT BROWN LIQUID | START | 4:39 |
| | STOP | 4:59 (26° C.) |
| Test #10: Evaluate 2.5% VM solubility in DI PROPYLENE GLYCOL | | |
| 75 mL 5.0% SOLUTION (150 mL DI PROPYLENE GLYCOL + 7.5 G VM) | | |
| 75 mL DI PROPYLENE GLYCOL | START | 5:05 PM |
| | STOP | 5:35 (26° C.) |
| TRANSPARENT/TRANSLUCENT BROWN LIQUID WITH 'FLECKS' | | |
| Test #11: Evaluate 5.0% VM solubility in an ester of Salicylic acid and a branched $C_{12}$ alcohol (HALLBRITE BHB) | | |
| 150 mL HALLBRITE BHB | START | 9:23 AM (22° C.) |
| 7.5 G OF VM | STOP | 9:50 (24° C.) |
| CARMEL BROWN | START | 9:51 |
| | STOP | 10:19 (24° C.) |
| Test #12: Evaluate 2.5% VM solubility in HALLBRITE BHB | | |
| 75 mL 5.0% (150 mL HALLBRITE BHB + 7.5 G VM) | START | 1:17 (22° C.) |
| 75 mL HALLBRITE BHB | STOP | 1:47 |
| CARMEL BROWN OPAQUE | | |

-continued

| Test #13: Evaluate 5.0% VM solubility in CITROFLEX 2 | | |
|---|---|---|
| 150 mL CITROFLEX 2 | START | 1:38 PM (22° C.) |
| 7.5 G OF VM | STOP | 2:12 (24° C.) |
|  | START | 2:13 |
| CARMEL BROWN OPAQUE | STOP | 3:07 (26° C.) |
| Test #14: Evaluate 2.5% VM solubility in CITROFLEX 2 | | |
| 75 mL 5% (150 ML CITROFLEX 2 + 7.5 G VM) | START | 3:18 PM |
| 75 mL CITROFLEX 2 | STOP | 3:44 (25° C.) |
| CARMEL BROWN OPAQUE | | |
| Test #15: Evaluate 5.0% VM solubility in CITROFLEX A-4 | | |
| 150 mL CITROFLEX A-4 | START | 1:47 PM (21° C.) |
| 7.5 G VM | STOP | 2:15 (25° C.) |
|  | START | 2:16 |
| CARMEL BROWN OPAQUE | STOP | 3:07 (26° C.) |
| Test #16: Evaluate 2.5% VM solubility in CITROFLEX A-4 | | |
| 75 mL 5.0% (150 mL CITROFLEX A-4 + 7.5 G VM) | | |
| 75 mL CITROFLEX A-4 | START | 3:18 PM |
|  | STOP | 3:44 (25° C.) |
| CARMEL BROWN OPAQUE | | |
| Test #17: Evaluate 5.0% VM solubility in DIBUTYL SEBACATE | | |
| 150 mL DIBUTYL SEBACATE | START | 4:21 PM (22° C.) |
| 7.5 G OF VM | STOP | 4:51 (25° C.) |
|  | START | 4:55 |
| Not successful | STOP | 5:25 |
| Test #18: Evaluate 2.5% VM solubility in DIBUTYL SEBACATE | | |
| 75 mL 5% SOLUTION (150 mL DBS + 7.5 G VM) | START | 5:29 PM |
| 75 mL DIBUYTL SEBACATE Not successful | STOP | 6:00 PM |
| Test #19: Evaluate 5.0% VM solubility in a diisononyl-cyclohexane dicarboxylate (HEXAMOL DINCH) | | |
| 150 mL HEXAMOL DINCH | START | 4:21 PM (22° C.) |
| 7.5 g OF VM | STOP | 4:51 (25° C.) |
| Not successful | START | 4:55 |
|  | STOP | 5:25 |
| Test #20: Evaluate 2.5% VM solubility in HEXAMOL DINCH | | |
| 75 mL 5% SOLUTION (150 mL HEXAMOL DINCH + 7.5 G VM) | | |
| 75 mL HEXAMOL DINCH | START | 5:29 PM |
|  | STOP | 6:00 PM |
| Test #21: Evaluate 5.0% VM solubility in DIPROPYLENE GLYCOL/ETHANOL | | |
| DIPROPYLENE GLYCOL 75 mL | START | 9:59 AM (21° C.) |
| ETHANOL (INDUSTRIAL) 75 mL | STOP | 10:25 (18° C.) |
| VM 7.5 G | START | 10:27 |
|  | STOP | 10:55 (18° C.) |
| TRANSLUCENT/BROWN LIQUID (MINIMAL SEDIMENT?) | | |
| Test #22: Evaluate 5.0% VM solubility in DIPROPYLENE GLYCOL/ETHANOL | | |
| DIPROPYLENE GLYCOL 100 mL | START | 9:59 AM (21° C.) |
| ETHANOL (INDUSTRIAL) 50 mL | STOP | 10:25 (21° C.) |
| VM 7.5 G | START | 10:27 |
|  | STOP | 10:55 (21° C.) |
| TRANSLUCENT BROWN LIQUID | | |
| Test #23: Evaluate VM solubility in DPG/ETHANOL | | |
| 75 mL 5% (75 mL DPG, 75 mL ETHANOL, 7.5 G VM) | | |
| 38 mL DPG | START | 11:05 |
| 38 mL ETHANOL | STOP | 11:40 |
| TRANSPARENT BROWN LIQUID - MAPLE SYRUP | | |
| Test #24: Evaluate VM solubility in DPG/ETHANOL | | |
| 75 mL 5% (100 mL DPG, 50 mL ETHANOL, 7.5 G VM) | | |
| 50 mL DPG | | |

-continued

| | | |
|---|---|---|
| 25 mL ETHANOL | START | 11:05 |
| | STOP | 11:40 |
| TRANSPARENT BROWN LIQUID - MAPLE SYRUP | | |

Test #25: Evaluate VM solubility in DPG/ETHANOL

| | | |
|---|---|---|
| 125 mL DPG | START | 11:55 (21° C.) |
| 25 mL ETHANOL | STOP | 12:24 (24° C.) |
| 7.5 G VM | START | 12:27 |
| | STOP | 12:56 (24° C.) |

Test #26: Evaluate VM solubility in ethoxylated acetylenic diols (SURFANOL 420)

| | | |
|---|---|---|
| 150 mL SURFANOL 420 | START | 12:40 (23° C.) |
| 7.5 G VM | STOP | 2:22 (28° C.) |
| OPAQUE BROWN LIQUID - VISCOUS WARM | | |

Test #27: Evaluate VM solubility in 75 mL 5% EVALUATE VM SOLUBILITY IN DPG/ETHANOL

| | | |
|---|---|---|
| 63 mL DPG (125 mL DPG, 25 ETHANOL, 75 G VM) | | |
| 13 mL ETHANOL | START | 12:50 |
| | STOP | 2:24 (24° C.) |
| TRANSPARENT BROWN LIQUID - MAPLE SYRUP | | |

Test #28: Evaluate VM solubility in ethoxylated acetylenic diols (SURFYNOL 420)

| | | |
|---|---|---|
| 75 mL 5% SOLUTION (150 mL SURFYNOL 420 + 7.5 G VM) | START | 2:40 |
| 75 mL SURFANOL 420 | STOP | 3:17 |
| OPAQUE BROWN LIQUID | | |

Test #29: Evaluate VM solubility in SURFYNOL 440

| | | |
|---|---|---|
| | START | 2:40 (24° C.) |
| 150 mL SURFYNOL 440 | STOP | 3:17 (25° C.) |
| 7.5 G VM | | |
| OPAQUE BROWN LIQUID | | |

Test #30: Evaluate 2.5% VM solubility in SURFYNOL 440

| | | |
|---|---|---|
| 75 mL 5% SOLUTION (150 mL SURFYNOL 440 + 7.5 G VM) | | |
| 75 mL SURFYNOL 440 | START | 3:22 PM |
| | STOP | 3:39 PM |
| OPAQUE BROWN LIQUID | | |

Test #31: Evaluate 5.0% VM solubility in SURFYNOL 465

| | | |
|---|---|---|
| 150 mL SURFYNOL 465 | START | 3:30 PM (22° C.) |
| 7.5 G VM | STOP | 3:59 (27° C.) |
| | START | 4:00 |
| | STOP | 4:32 |
| OPAQUE BROWN LIQUID | | |

Test #32: Evaluate 2.5% VM solubility in SURFYNOL 465

| | | |
|---|---|---|
| 75 mL 5% SOLUTION (150 mL SURFYNOL 465 + 7.5 G VM) | | |
| 75 mL SURFYNOL 465 | START | 4:35 |
| | STOP | 5:05 |
| OPAQUE BROWN LIQUID | | |

Test #33: Evaluate VM solubility in SURFYNOL 485

| | | |
|---|---|---|
| 150 mL SURFYNOL 485 | START | 10:00 AM (23° C.) |
| 7.5 G VM | STOP | 10:30 (29° C.) |
| | START | 10:32 |
| | STOP | 11:06 (30° C.) |
| OPAQUE BROWN LIQUID | | |

Test #34: Evaluate VM solubility in DPG/CITROFLEX 2

| | | |
|---|---|---|
| 75 mL DPG | | |
| 75 mL CITROFLEX 2 | START | 10:05 (21° C.) |
| 7.5 G VM | STOP | 10:32 (24° C.) |
| | START | 10:33 |
| | STOP | 11:06 (26° C.) |
| TRANSPARENT BROWN LIQUID, NO IMMEDIATE SEPARATION | | |

Test #35: Evaluate VM solubility in SURFYNOL 485

| | | |
|---|---|---|
| 75 mL 5% (150 mL SURFYNOL 485 + 7.5 G VM) | START | 11:15 |

| | | |
|---|---|---|
| 75 mL SURFYNOL 485 | STOP | 11:50 |
| OPAQUE BROWN LIQUID | | |

Test #36: Evaluate VM solubility in DPG/CITROFLEX 2

| | | |
|---|---|---|
| 75 mL 5% (75 mL DPG, 75 mL CITROFLEX 2, 7.5 G VM) | START | 11:15 |
| | STOP | 11:50 |
| 38 mL DPG | | |
| 38 mL CITROFLEX 2 | | |
| TRANSPARENT BROWN LIQUID - MINIMAL SEDIMENT/FLECKS | | |

Test #37: Evaluate 7.5% VM solubility in DPG/CITROFLEX 2 (1:1)

| | | |
|---|---|---|
| 75 mL DPG | START | 12:19 PM (21° C.) |
| 75 mL CITROFLEX 2 | STOP | 12:59 (25° C.) |
| 11.25 G VM | START | 1:01 PM |
| | STOP | 1:30 |
| | START | 1:31 |
| | STOP | 2:15 (25° C.) |
| (TRANSLUCENT @ ~1:00) | | |
| TRANSLUCENT @~1:30 | | |
| TRANSLUCENT BROWN LIQUID | | |

Test #38: Evaluate VM solubility in ETHANOL/CITROFLEX 2 1:1

| | | |
|---|---|---|
| 75 mL ETHANOL | START | 11:02 AM (17° C.) |
| 75 mL CITROFLEX 2 | STOP | 11:46 (18° C.) |
| 11.25 G VM | START | 11:49 |
| | STOP | 12:11 (18° C.) |
| TRANSPARENT BROWN LIQUID | | |

Test #39: Evaluate VM solubility in ETHANOL/CITROFLEX 2, 1:1

| | | |
|---|---|---|
| 75 mL ETHANOL | START | 11:02 AM (17° C.) |
| 75 mL CITROFLEX 2 | STOP | 11:46 (18° C.) |
| 7.5 G VM | START | 11:49 |
| | STOP | 12:11 (18° C.) |
| TRANSPARENT BROWN LIQUID | | |
| VISUAL INSPECTION OF WELL SETTLED (>2 DAYS) SAMPLES (CLEAR UNLESS SPECIFIED) | | |
| 7.5% VM IN ETHANOL (LAB GRADE) D. BROWN WITH 7.5 CM SED | | |
| 7.5% VM IN ETHANOL (INDUSTRIAL) D. BROWN WITH 7.5 CM SED | | |
| 5.0% VM IN ETHANOL (INDUSTRIAL) BROWN WITH .25-.5 CM SED | | |
| 2.0% VM IN ETHANOL (INDUSTRIAL) BROWN | | |
| 5.0% VM IN HALLBRITE OS HONEY BROWN .25-.5 CM SED | | |
| 2.5% VM IN HALLBRITE OS HONEY BROWN .25-.5 CM SED | | |
| 5.0% VM IN PROPYLENE GLYCOL BROWN .25-.5 CM SED | | |
| 2.5% VM IN PROPYLENE GLYCOL BROWN 7.5 CM SED | | |
| 5.0% VM IN DI PROPYLENE GLYCOL BROWN <.25 CM SED | | |
| 2.5% VM IN DI PROPYLENE GLYCOL BROWN SPECKS SED | | |
| 5.0% VM IN HALLBRITE BHB (BUTYLOCTYL SALICYLATE) PALE HONEY BROWN <.25 CM SED | | |
| 2.5% VM IN HALLBRITE BHB PALE HONEY BROWN >.5 CM SED | | |
| 5.0% VM IN CITROFLEX 2 BROWN <.25 CM SED | | |
| 2.5% VM IN CITROFLEX 2 BROWN >.5 CM SED | | |
| 5.0% VM IN CITROFLEX A4 HONEY BROWN TRANSLUCENT .25-.5 CM SED | | |
| 2.5% VM IN CITROFLEX A4 HONEY BROWN TRANSLUCENT >.5 CM SED | | |
| 5.0% VM IN DEBS TRANSLUCENT HONEY BROWN >.5 CM SED | | |
| 2.5% VM IN DBS TRANSLUCENT HONEY BROWN >.5 CM SED | | |
| 5% SAMPLES MAY SEEM TO HAVE LESS SED DUE TO SAMPLING AND SERIAL DILUTION TO GET 2.5% | | |

VISUAL INSPECTION OF WELL
SETTLED (>2 DAY) SAMPLES (CLEAR
UNLESS SPECIFIED)
5% VM IN HEXAMOL DINCH PALE
HONEY BROWN (cyclohexane carboxylic
acid ester) >.5 CM SED
2.5% VM IN HEXAMOL DINCH PALE
HONEY BROWN >.5 CM SED
5.0% VM IN 1:1 DI PROPYLENE GLYCOL/
ETHANOL D. BROWN <.25 SED
2.5% VM IN 1:1 DPG/ETHANOL BROWN
*MINIMAL SED
5.0% VM IN 2:1 DPG/ETHANOL BROWN
>.25 CM SED
2.5% VM IN 2:1 DPG/ETHANOL BROWN
~ZERO SED
125/25 5.0% VM IN 5:1 DPG/ETHANOL
BROWN >.25 CM SED
2.5% VM IN 5:1 DPG/ETHANOL BROWN
~ZERO SED
5:1? 5.0% VM IN SURFYNOL 420
TRANSLUCENT BROWN .25-.5 CM SED
2.5% VM IN SURFYNOL 420
TRANSLUCENT BROWN >.5 CM SED
5.0% VM IN SURFYNOL 440
TRANSLUCENT BROWN >.5 CM SED
2.5% VM IN SURFYNOL 440
TRANSLUCENT BROWN >.5 CM SED
5.0% VM IN SURFYNOL 465
TRANSLUCENT BROWN .25-.5 CM SED
2.5% VM IN SURFYNOL 465
TRANSLUCENT BROWN .25-.5 CM SED
VISCOUS 5.0% VM IN SURFYNOL 485
OPAQUE CARMEL BROWN ~ZERO
VISCOUS 2.5% VM IN SURFYNOL 485
OPAQUE CARMEL BROWN ~ZERO
7.5% VM IN 1:1 DPG/CITROFLEX 2
TRANSLUCENT D. BROWN >.5 CM SED
5.0% VM IN 1:1 DPG/CITROFLEX 2
TRANSPARENT BROWN SPECKS SED
2.5% VM IN 1:1 DPG/CITROFLEX 2
TRANSPARENT BROWN ~0 SED
*MINIMAL = VISIBLE BUT NOT
COVERING CENTER OF BOTTOM OF
JAR
LIQUID LACTROL FORMULATION
DEVELOPMENT Test #40: Evaluate VM solubility in 2:1 ETHANOL/CITROFLEX 2

| | | |
|---|---|---|
| 100 mL ETHANOL (INDUSTRIAL GRADE) | START | 10:46 AM (19° C.) |
| 50 mL CITROFLEX 2 | STOP | 11:15 (20° C.) |
| 7.5 G VM | START | 11:17 AM |
| | STOP | 11:46 AM (NA) |
| BROWN TRANSPARENT LIQUID <.25 CM SED | | |

Test #41: Evaluate VM solubility in 2:1 CITROFLEX 2/ETHANOL

| | | |
|---|---|---|
| 100 mL CITROFLEX 2 | START | 10:46 AM (19° C.) |
| 50 mL ETHANOL | STOP | 11:15 (20° C.) |
| 7.5 G VM | START | 11:17 AM |
| | STOP | 11:46 (20° C.) |
| BROWN TRANSPARENT LIQUID, NO SED | | |

Test #42: Evaluate VM solubility in 3:1 ETHANOL/CITROFLEX 2

| | | |
|---|---|---|
| 112 mL ETHANOL (INDUSTRIAL GRADE) | START | 12:16 PM (20° C.) |
| 38 mL CITROFLEX 2 | STOP | 1:40 PM (19° C.) |
| 7.5 G VM | | |
| BROWN TRANSPARENT LIQUID .25-.5 CM SED | | |

Test #43: Evaluate VM solubility in 3:1 CITROFLEX 2/ETHANOL

| | | |
|---|---|---|
| 112 mL CITROFLEX 2 | | |
| 38 mL ETHANOL (INDUSTRIAL GRADE) | START | 12:16 PM (19° C.) |
| 7.5 G VM | STOP | 1:40 PM (21° C.) |
| BROWN TRANSPARENT LIQUID NO SED | | |

| -continued |||
|---|---|---|
| Test #44: Evaluate VM solubility in 2:1 CITROFLEX 2/ETHANOL |||
| 100 mL CITROFLEX 2 | START | 2:10 PM (19° C.) |
| 50 mL ETHL (INDUSTRIAL GRADE) | STOP | 2:44 PM (20° C.) |
| 11.25 G VM | START | 2:50 PM |
| | STOP | 3:10 |
| UNDISSOLVED VM AFTER 1 HOUR | START | 3:15 |
| | STOP | 3:50 PM |
| Test #45: Evaluate VM solubility in 3:1 CITROFLEX 2/ETHANOL |||
| 112 mL CITROFLEX 2 | | |
| 38 mL ETHANOL (INDUSTRIAL GRADE) | START | 2:10 (19° C.) |
| 11.25 G VM | STOP | 2:44 (20° C.) |
| | START | 2:50 |
| UNDISSOLVED VM AFTER 1 HOUR | STOP | 3:10 |
| | START | 3:15 |
| | STOP | 3:50 |
| Test #46: Evaluate VM solubility in 4:1 CITROFLEX 2/ETHANOL |||
| 120 mL (136.32 G)* CITROFLEX 2 | START | 4:09 |
| 30 mL (23.7 G)* ETHANOL | STOP | 4:39 (19° C.) |
| 7.5 G VM | START | 4:41 (20° C.) |
| | STOP | 5:09 |
| TRANSPARENT BROWN LIQUID, SPECKS OF SED | | |
| Test #47: Evaluate VM solubility in 4:1 CITROFLEX 2/ETHANOL |||
| 120 mL (136.32 G)* CITROFLEX 2 | START | 4:09 (19° C.) |
| 30 mL (23.7 G)* ETHANOL | STOP | 4:39 (21° C.) |
| 11.25 G VM | START | 4:41 |
| | STOP | 5:39 |
| OPAQUE D. BROWN LIQUID NO IMMEDIATE SEDIMENT *SPECIFIC GRAVITY = CITROFLEX 2 = 1.136 ETHANOL = .790 | | |
| Test #48: Evaluate 6% VM solubility in VM IN 1:1 CITROFLEX 2:ETHANOL |||
| 85.2 GM CITROFLEX 2 | START | 9:50 |
| 59.25 GM ETHANOL | STOP | 11:10 |
| 9.0 GM VM | | |
| * SIGNIFICANT FALLOUT .25-.5 CM SED | | |
| Test #49: Evaluate 6% VM solubility in 2:1 CITROFLEX 2:ETHANOL |||
| 113.6 GM CITROFLEX 2 | START | 9:50 |
| 39.5 GM ETHANOL | STOP | 11:10 |
| 90 GM VM | | |
| STABLE AFTER 30 MINUTES - <.25 CM SED | | |
| Test #50: Evaluate 6% VM solubility in 3:1 CITROFLEX 2:ETHANOL |||
| 127.23 GM CITROFLEX 2 | START | 11:32 |
| 30.20 GM ETHANOL | STOP | 12:50 |
| 9.0 GM OF VM | | |
| >.5 CM SED | | |
| Test #51: Evaluate 6% VM solubility in 1:1 CITROFLEX 2:DPG |||
| 76.65 GM DPG | START | 11:32 |
| 85.2 GM CITROFLEX 2 | STOP | 12:50 |
| 9.0 GM VM | | |
| CLEAR WHEN TAKEN OFF AGITATOR MINIMAL SPECKS SEDS | | |
| Test #52: Evaluate 6% VM solubility in 2:1 CITROFLEX:DPG |||
| 51.1 GM DPG | START | |
| 113.6 GM CITROFL 2 | | |
| 9.0 GM VM | | |
| CLOUDY WHEN TAKEN OFF AGITATOR OPAQUE D. BROWN MINIMAL SPECKS SED | | |
| Test #53: Evaluate 6% VM solubility in 3:1 CITROFLEX 2:DPG |||
| 38.32 GM DPG | | |
| 127.23 GM CITROFLEX 2 | | |
| 9.0 GM VM | | |
| CLOUDY WHEN TAKEN OFF AGITATOR | | |

| OPAQUE D. BROWN <.25 CM SED SOLUTION INSPECTION RESULTS | | |
|---|---|---|
| | ROOM TEMP | 8° C. |
| 5% VM IN 1:1 CITROFLEX 2:ETHANOL | VERY MINOR DEPOSIT | VERY MINOR |
| 5% VM IN 2:1 ETHANOL:CITROFLEX 2 | MINOR DEPOSIT | MINOR DEPOSIT |
| 5% VM IN 2:1 CITROFLEX 2:ETHANOL | VERY MINOR DEPOSIT | VERY MINOR |
| 5% VM IN 3:1 ETHANOL:CITROFLEX 2 | SIGNIFICANT DEP | SIGNIFICANT |
| 5% VM IN 3:1 CITROFLEX 2:ETHANOL | VERY MINOR HAZE | MINOR HAZE |
| 7.5% VM IN 2:1 CITROFLEX 2:ETHANOL | SIGNIFICANT DEPOSIT | N/A |
| 7.5% VM IN 3:1 CITROFLEX 2:ETHANOL | SIGNIFICANT DEP | N/A |
| 5% VM IN 4:1 CITROFLEX 2:ETHANOL | MODERATE DEP | N/A |
| 7.5% VM IN 4:1 CITROFLEX 2:ETHANOL | SIGNIFICANT DEP | N/A |
| *1 = COMPLETELY STABLE | | |
| 2 = MINOR HAZE | | |
| 3 = MODERATE DEPOSIT | | |
| 4 = SIGNIFICANT DEPOSIT | | |
| 5% VM IN 1:1 DPG:CITROFLEX 2 | STABLE WO DEP | N/A |
| 6% VM IN 1:1 CITROFLEX 2:ETHANOL | MODERATE DEP | N/A |
| 6% VM IN 2:1 CITROFLEX 2:ETHANOL | SLIGHT HAZE | |
| 6% VM IN 3:1 CITROFLEX 2:ETHANOL | | |
| VISUAL INSPECTION AFTER OVERNIGHT SETTLING | | |
| 6.0% 1:1 CITROFLEX 2/ETHANOL <.25 CM SED. TRANSPARENT | | |
| 6.0% 2:1 CITROFLEX 2/ETHANOL <.25 CM SED, TRANSPARENT | | |
| 6.0% 3:1 CITROFLEX 2/ETHANOL >.5 CM SED, TRANSPARENT | | |
| 6.0% 1:1 CITROFLEX 2/DPG SPECKS OF SED, TRANSPARENT | | |
| 6.0% 2:1 CITROFLEX 2/DPG <.25 CM SED, TRANSLUCENT | | |
| 6.0% 3:1 CITROFLEX 2/DPG .25-.5 CM SED, TRANSLUCENT SAMPLE FOR FRIDE | | |
| 7.5% 2:1 CITROFLEX 2/ETHANOL >.5 CM SED, TRANSPARENT | | |
| 7.5% 3:1 CITROFLEX 2/ETHANOL >.5 CM SED, TRANSPARENT | | |
| 7.5% 4:1 CITROFLEX 2/ETHANOL >.5 CM SED, TRANSPARENT | | |
| AT 7.5% ALL HAD SIGNIFICANT SEDIMENT | | |
| AT 6.0% THE 1:1 CITROFLEX 2/DPG HAD ONLY SPECKS | | |
| AT 6.0% ALL CITROFLEX 2/ETHANOLS HAD SEDIMENT | | |
| 5.0 1:1 C/E MINIMAL | | |
| 2:1 >.25 CM | | |
| 3:1 .25-.5 CM | | |
| 2:1 DPG W/CITROFLEX BY WEIGHT W/CALC - TRY BY END OF WEEK | | |
| 3:1 DPG | | |
| 7.5% ETHYL LACTATE - DARK BROWN CLEAR LIQUID MINIMAL SETTLING | | |
| 10% ETHYL LACTATE DARK BROWN CLEAR LIQUID <.25 CM SETTLING | | |

Preferred formulations include:

92-10 (identifying code), a 5% VM in 1:1:0.05:0.3 parts by weight solution of ethyl lactate, ethanol, ethyl acetate, and triethyl citrate.

5-10, a 7.5% VM in ethyl lactate.

7-10, a 7.5% VM in 1:0.2 parts by weight solution of ethyl lactate and triethyl citrate.

24-10, a "5-10" formulation with 6% polysorbate 80.

43-10, a 6.3% VM in 1:1 parts by weight solution of ethyl lactate and dipropylene glycol.

44-10, a 6.3% VM in 1:1:0.5 parts by weight solution of ethyl lactate, dipropylene glycol, and polysorbate 80.

45-10, a 6.3% VM in 1:1:0.5 parts by weight solution of ethyl lactate, dipropylene glycol, and triethyl citrate.

59-10, a 6.3% VM in 1:1:0.5 parts by weight solution of ethyl lactate, dipropylene glycol, and Tween 20 surfactant.

63-10, a 6.3% VM in 1:1:0.31 parts by weight solution of ethyl lactate, dipropylene glycol, and polysorbate 80.

65-10, a 6.3% VM in 1:1:1 parts by weight solution of ethyl lactate, dipropylene glycol, and triethyl citrate.

98-10, a 6.3% VM in 1:10.2 parts by weight solution of ethyl lactate and triethyl citrate.

EXAMPLE 3

The purpose of this experiment was to determine any detrimental effects of soluble formulations of virginiamycin with additives on yeast growth and ethanol production in real corn mash fermentations. Yeasts were coinoculated with a consortium of *Lactobacillus* sp bacteria in improperly mixed fermentors. The soluble formulations of virginiamycin ("VM") that were tested included:

Sample "5DPGCit": 5.0% w/w active VM (7.5 g) in 1:1 by volume dipropylene glycol Dipropylene Glycol (76.65 g):Citroflex™ 2 (85.2 g) (4.4% by weight).

Sample "5CitEth": 5.0% w/w active VM (7.5 g) in 1:1 by volume Citroflex™ 2 (85.2 g): ethanol (59.25 g) (4.9% by weight).

Sample "2.5Eth(2)DPG(1)": 2.5% w/w active VM (3.75 g) 1:1 by volume ethanol Ethanol (59.25 g):dipropylene glycol Dipropylene Glycol (76.65 g) (2.7% by weight).

Sample "5DPGCit": 5.0% w/w active VM (7.5 g) in 1:1 by volume Dipropylene Glycol (76.65 g):Citroflex™ 2 (85.2 g) (4.4% by weight).

Sample "5CitEth": 5.0% w/w active VM (7.5 g) in 1:1 by volume Citroflex™ 2 (85.2 g):Ethanol (59.25 g) (4.9% by weight).

Sample "2.5Eth(2)DPG(1)": 2.5% w/w active VM (3.75 g) 1:1 by volume Ethanol (59.25 g):Dipropylene Glycol (76.65 g) (2.7% by weight).

Preparation of corn mash (Gelatinization, Liquefaction, Saccharification): Sacks of yellow dent #2 corn (25 kg) was acquired from Early's feed (Saskatoon, SK, Canada), and frozen at −40° C. for a week to destroy any insects and eggs that may be present. An aliquot of corn (10 kg) was ground once in a S500 Disk Mill (Glen Mills Inc., Clifton, N.J.) at setting #5 and stored frozen until the next day. Reverse osmosis (RO) water (17.5 L) was added to a 59 L pilot plant steam kettle and heated to 60° C., followed by a 30 ml volume of Spezyme™ Ethyl alpha amylase (Genencor, Rochester, N.Y.). The ground corn was then added slowly with constant vigorous mixing with a motorized paddle. This mixing was maintained throughout the mashing procedure.

The temperature in the steam kettle was incrementally increased from 60° C. to 96° C. in 10° C. increments with a 5 minute hold time at each increment. Once 96° C. was reached, the mixture was held for 60 minutes (to insure complete gelatinization) and then cooled to 83° C. A second 30 ml dose of Spezyme™ Ethyl alpha amylase was added and the temperature maintained at 83° C. for 60 minutes. The mash temperature was then decreased to 60° C. at which point 2 L RO water and 200 ml G-Zyme™ 480 Ethanol glucoamylase (Genencor, Rochester, N.Y.) were added. The mash was allowed to saccharify for 60 minutes. Aliquots of mash (4500 g) were dispensed into 5 pre-weighed 7.6 L polypropylene containers (containing large solid glass mixing marbles) and then autoclaved for 1.5 hours at 121° C. and 15 PSI.

Tests for mash sterility were confirmed by incubating aliquots of mash for 5 months at room temperature and determining bacterial contamination with microbiological spread plates onto MRS media. No bacterial contamination was detected in all test incubated mashes.

For the mash calibration, all containers and manipulations involving aliquots of mash were weighed in order to calculate the required amount of sterile RO water to be added to each 7.6 L sterile container of mash to achieve 26% w/v dissolved solids. For each 7.6 L sterile container of mash, a 60 g aliquot was removed and divided into two 30 g subsamples within 50 ml centrifuge tubes. To one subsample, 10 ml RO water was added. After thorough mixing, both subsamples were centrifuged (10K RPM, 4° C., 20 minutes) in a Sorvall RC-5C centrifuge (Sorvall Instruments, Wilmington, Del.). The liquid supernatants were removed, and further clarified through Whatman 934-AH glass microfiber filters (Clifton, N.J.). The specific gravity of each subsample was then determined using a digital density meter (DMA-45; Anton Paar KG, Graz, Austria) which was temperature regulated to 4° C. An additional volume of sterile DO water that is required in each 7.6 L container to bring the dissolved solids concentration to 26% w/v. These aliquots of sterile RO water were added aseptically to each container and vigorously mixed. The mash from each 7.6 L container was then aseptically dispensed into sterile 1.9 L containers (1500 g aliquots), labeled with the mash batch number, date, and mash concentration, and frozen until needed. An accurate liquid volume was used in all calculations involving concentrations of added substances to the fermentor since approximately 30% of the total volume in the fermentor is insoluble material and does not participate as a solvent for dissolving chemicals.

For all bacterial experiments, a consortium of 6 industrially isolated and relevant *Lactobacilli* spp cultures were used. Three of the cultures (Coded: 18A, Rix20, Rix21) are representative of *Lactobacilli* frequently isolated from North American fuel ethanol plants. The remainder (coded: Rix22, Rix83, Rix84), are *Lactobacilli* isolated from the field, but are not frequently found at fuel ethanol plants and exhibit stronger growth characteristics and higher fermentation stress tolerances. This experimental design using a consortium of bacteria better reflects the real world bacterial contamination occurring at an fuel ethanol plant, which is never a pure culture. Furthermore, using the "heartier" *Lactobacilli*, provided the experiments with a "worst-case" scenario of contamination.

For four of the bacterial cultures (18A, Rix20, Rix21, Rix22), a loop of each was taken from a master slant and inoculated into a 250 ml Klett flask containing 100 ml MRS broth. For two of the bacterial cultures (Rix83, Rix84), 3 triplicate master slants were "washed" with either MRS broth (Rix83), or YEPD broth (Rix84) and made up to a volume of 50 ml in respective Klett flasks and media. The headspace of all flasks were then flushed with sterile $CO_2$ for 1 minute. The cultures were incubated overnight in a rotary incubator at 30° C. at 150 RPM. The following morning the Klett reading of each culture was determined. If a Klett value for a particular culture was below 150, then the culture was pelleted by centrifugation, a volume of supernatant liquid was removed, and the pelleted culture re-suspended in the remaining volume to give a more concentrated culture. Once all cultures showed a Klett value >150, then each culture was diluted accurately to 150 Klett, and subsequently diluted so that a 10 ml aliquot of each culture into a fermentor (with the fermentor liquid volume known), will contain a desired initial concentration (CFU/ml) of 1E6 CFU/ml.

To achieve a 5E7 CFU/ml level of inoculation in each fermentor, 5.763 g of Ethanol Red ADY™ was directly pitched into each fermentor at the appropriate time. To each of 5 pre-sterilized Bioflo III fermentors (New Brunswick Scientific, Edison, N.J.), 4 L sterile mash was aseptically added. Agitation (when on) was set for 150 RPM.

The pH of the fermentors were not controlled and had an initial value of 4.6 (after addition of all chemicals). Once 32° C. was reached in the fermentors, the headspace of each fermentor was purged with sterile CO2 at 40 ml/min for 30 minutes to ensure that the entire fermentor (headspace and liquid) was anaerobic for inoculation. The purging was also continued during fermentation to maintain anaerobic conditions. The bacterial inocula was then added and allowed to adjust for 1 hour to the fermentor conditions. The yeast was then added at this time and allowed to inculate for 30 minutes. Following this, the addition of vm (in whatever form) was added to the appropriate fermentor to start the experiment.

For the additions of all forms of vm, the amount of product to be added to each respective fermentor were calculated based on giving active vm concentrations (ppm) in all fermentors. All dosings of VM were calculated based on the total volume of the fermentor and was added by weight. To each fermentor was added: 10 ml 0.2 μm filter-sterilized Urea stock solution (8 mM urea in liquid volume in the fermentors); 60 ml (6×10 ml) Bacterial inocula, and 40 ml sterile DO water (as the difference). At the time of sampling, the agitation in the fermentors were turned on for 10 seconds at 150 RPM to mix the contents of the fermentor, the appropriate samples were taken, and then the mixing was turned off until the subsequent sampling time.

The improperly mixed fermentors simulate the conditions found in field ethanol plants where it is not uncommon for fermentors to not be mixed properly (residence times vary from 1 hour to 12 hours depending on flow and fermentor sizes), or have sediments and biofilms where antimicrobial chemicals cannot easily reach.

Samples from the fermentors were sampled (33 ml) at 0, 6, 12, 24, 36, and 48 h. All samples were placed on ice to prevent growth. An 11 ml aliquot of each sample was serially diluted in 0.1% w/v sterile peptone water, and microbiologically plated onto MRS+C agar in duplicate. All plates were incubated for 48 h at 30° C. in an anaerobic CO2 incubation chamber, and manually enumerated for viable *Lactobacilli*. The remaining 22 ml aliquot of each sample was centrifuged (10K RPM, 4° C., 20 minutes) in a Sorvall RC-5C centrifuge. The liquid supernatant was then passed through a 0.2 μm membrane filter to remove any particulates and frozen for future analysis. Lactic acid, glycerol, ethanol, acetic acid, and glucose concentrations were determined by HPLC analysis. The samples were thawed and diluted to the required extent with Milli-Q water. Aliquots of the diluted samples (1 ml) were each mixed with an equal volume of 2% w/v boric acid (internal standard), and injected into a Biorad HPX-87H Aminex column equilibrated at 40° C. The eluent was 5 mM sulfuric acid flowing at a rate of 0.5 ml/min.

Results are presented in the Tables below, in order of Control (0 ppm), Control #2 (0.5 ppm VM powder), 5DPGCit (0.5 ppm VM predissolved in dipropylene glycol/citroflex), 5CitEth (0.5 ppm VM predissolved in ethanol/citroflex), and 2.5Eth(2)DPG(1) (0.5 ppm VM predissolved in dipropylene glycol/ethanol).

|  | Control (0 ppm) | Control#2 (0.5 ppm VM) | 5DPGCit | 5CitEth | 2.5Eth(2)DPG (1) |
|---|---|---|---|---|---|
| Yeast counts (xE8) | | | | | |
| 0 hours | 0.8 | 0.8 | 0.8 | 0.8 | 0.8 |
| 6 hours | 0.7 | 0.7 | 0.7 | 0.7 | 0.7 |
| 12 hours | 2 | 2 | 3 | 2 | 2 |
| 24 hours | 6 | 5 | 6 | 4 | 5 |
| 36 hours | 5 | 5 | 5 | 5 | 5 |
| 48 hours | 5 | 5 | 5 | 4 | 4 |
| Lactobaccilli (xE7) | | | | | |
| 0 hours | 0.1 | 0.2 | 0.1 | 0.09 | 0.08 |
| 6 hours | 1 | 0.4 | 0.2 | 0.5 | 0.08 |
| 12 hours | 7 | 2 | 0.4 | 0.9 | — |
| 24 hours | 15 | 2 | — | 2 | — |
| 36 hours | 20 | 3 | 0.9 | 2 | — |
| 48 hours | 10 | 2 | — | 3 | — |
| Lactic acid (% wt/v) | | | | | |
| 0 hours | 0.01 | 0.01 | 0.01 | 0.01 | 0.01 |
| 6 hours | 0.02 | 0.01 | 0.01 | 0.01 | 0.01 |
| 12 hours | 0.05 | 0.03 | 0.02 | 0.03 | 0.02 |
| 24 hours | 0.075 | 0.04 | 0.03 | 0.04 | 0.02 |
| 36 hours | 0.17 | 0.09 | 0.06 | 0.08 | 0.04 |
| 48 hours | 0.19 | 0.11 | 0.07 | 0.1 | 0.04 |
| Ethanol (% wt/v) | | | | | |
| 0 hours | 0.1 | 0.1 | 0.1 | 0.1 | 0.1 |
| 6 hours | 1 | 1 | 1 | 0.9 | 0.9 |
| 12 hours | 3.9 | 3.9 | 3.9 | 4 | 4 |
| 24 hours | 6.8 | 7.2 | 7.1 | 7.2 | 7.2 |
| 36 hours | 8.4 | 9.2 | 8.6 | 8.8 | 8.8 |
| 48 hours | 9.6 | 10 | 9.6 | 9.9 | 9.9 |
| Glucose (% wt/v) | | | | | |
| 0 hours | 20.5 | 21 | 20 | 20.5 | 21 |
| 6 hours | 19 | 19.5 | 19.3 | 19.3 | 19.7 |
| 12 hours | 13 | 13.5 | 13 | 13 | 13 |
| 24 hours | 6.5 | 6.5 | 6.5 | 6.5 | 6.5 |
| 36 hours | 1 | 1 | 1 | 1 | 1 |
| 48 hours | 0 | 0 | 0 | 0 | 0 |

The greatest control of *lactobacilli* occurred in samples treated with VM dissolved in 1:1 by volume Citroflex™ and dipropylene glycol. Interestingly, greatest reduction of lactic acid production was found with 2.5% VM in dipropylene glycol and ethanol, though samples treated with VM dissolved in 1:1 by volume Citroflex™ and dipropylene glycol came in second.

EXAMPLE 4

The purpose of this experiment was to determine the efficacy of soluble formulations of VM in real corn mash fermentations against a consortium of *Lactobacillus* sp bacteria in improperly mixed fermentors. Similar VM formulations as described in the previous Example were used. In this experiment no yeasts were added, to allow a more accurate determination of VM efficacy on bacteria since the additional synergistic negative effects of yeast (on bacterial growth) is eliminated.

The samples tested were similar to those used in the previous example.
Control—no VM
Control #2—0.5 ppm VM added as powdered Lactrol™ (Phibro Animal Health Corp, Ridgview, N.J.).
  5DPGCit—providing 0.5 ppm VM.
  6DPGCit—(9.0 g VM+85.2 g Citroflex2+76.65 g Dipropylene Glycol, 5.3% by wt.) providing 0.5 ppm VM.
  5CitEth—(7.5 g VM+85.2 g Citroflex2+59.25 g Ethanol) providing 0.5 ppm VM.
Results are shown below.

| Lactobaccilli (xE7) | Control (0 ppm) | Control#2 (0.5 ppm VM) | 5DPGCit | 6DPGCit | 5CitEth |
|---|---|---|---|---|---|
| 0 hours | 0.1 | 0.15 | 0.1 | 0.09 | 0.08 |
| 6 hours | 0.8 | 0.5 | 0.1 | 0.15 | 0.4 |
| 12 hours | 12 | 2 | 0.4 | 0.8 | 1 |
| 24 hours | 130 | 80 | 6 | 40 | 20 |
| 36 hours | 120 | 100 | 50 | 80 | 60 |
| 48 hours | 110 | 110 | 105 | 100 | 110 |

These tests clearly showed the benefits provided by predissolved VM added to poorly mixed fermentators. The effect is greatest in the 6 to 24 hour time frame, as would be expected as even in a poorly mixed fermentator VM powder will eventually dissolve. 5DPGCit. That is, 5% w/v VM in equal volumes of Citroflex™ and Dipropylene glycol, provided the best performance, followed by 5 CitEth. The 6DPGCit performed less well, suggesting the VM was not fully solubilized at 6% w/v when these solvents are used.

EXAMPLE 5

The purpose of this experiment was to determine the efficacy of soluble formulations of VM in real corn mash fermentations against a consortium of *Lactobacillus* sp bacteria in improperly mixed fermentors. In these tests, the amount of VM was reduced to the lowest practical limits. Similar VM formulations as described in the previous Example were used. In this experiment no yeasts were added, to allow a more accurate determination of VM efficacy on bacteria since the additional synergistic negative effects of yeast (on bacterial growth) is eliminated.

The samples tested were similar to those used in the previous example.
Control #1: No VM
Control #2: 0.5 ppm active VM in the mash, added as fine powder.
5.0% w/v active VM in 1:1 Dipropylene Glycol:Citroflex2 "5DPGCit" at 0.39 ppm active VM in the mash.
5.0% w/v active VM in 1:1 Citroflex 2:Ethanol "5CitEth" at 0.37 ppm active VM in the mash.

6.0% w/v active VM in 1:1 Dipropylene Glycol:Citroflex2 "6DPGCit" at 0.37 ppm active VM in the mash.

Preparation of the mash and fermentators was identical to those described in the previous experiment. An oversight in how the formulation were constructed (by % w/w) and how the formulations were added to the fermentors (by % w/v) resulted in concentrations of active vm that were lower in all fermentors than the desired 0.5 ppm.

All additions of vm (regardless of concentration) resulted in decreased concentrations of lactic acid from the bacteria. Even with the reduced ppm active vm concentrations, all formulations did provide more control of the bacteria consortium than the control—especially during the first 24 hours into the fermentation. None of the formulations at the concentrations tested resulted in more control of the bacterial consortium than the 0.5 ppm Lactrol control. This is primarily attributed in the reduced dosages achieved in the fermentors. Of all formulations tested in this round, 5CitEth (at 0.37 ppm active VM) provided the best control of the bacterial consortium as it more closely approached the 0.5 ppm Lactrol control profile.

| | Control (0 ppm) | Control#2 powder (0.5 ppm VM) | 5DPGCit (0.39 ppm) | 6DPGCit (0.37 ppm) | 5EthCit (0.37 ppm) |
|---|---|---|---|---|---|
| Lactobaccilli (xE7) | | | | | |
| 0 hours | 0.07 | 0.09 | 0.08 | 0.08 | 0.08 |
| 6 hours | 1 | 0.03 | 0.4 | 0.03 | 0.03 |
| 12 hours | 9 | 1 | 4 | 1 | 1 |
| 24 hours | 100 | 10 | 70 | 10 | 10 |
| 36 hours | — | 70 | 70 | 70 | 70 |
| 48 hours | — | 90 | 80 | 90 | 90 |
| Lactic acid (% wt/v) | | | | | |
| 0 hours | 0.01 | 0.01 | 0.01 | 0.01 | 0.01 |
| 6 hours | 0.01 | 0.01 | 0.01 | 0.01 | 0.01 |
| 12 hours | 0.09 | 0.02 | 0.04 | 0.05 | 0.02 |
| 24 hours | 0.42 | 0.2 | 0.41 | 0.38 | 0.31 |
| 36 hours | 0.78 | 0.57 | 0.62 | 0.63 | 0.58 |
| 48 hours | 0.96 | 0.73 | 0.8 | 0.8 | 0.73 |

EXAMPLE 6

Mash was prepared as discussed previously, placed in poorly mixed fermentators, and treated with the following:

Nothing (Control #1)

Lactrol powder sufficient to provide 0.5 ppm VM in mash.

2% w/v (2.5% by wt) active VM in EtOH (3 g VM+118.5 g (150 ml) Ethanol) sufficient to provide 0.47 ppm VM in mash 2.5% w/v (2.5% by wt) active VM in DPG (3.75 g VM+153.3 g (150 ml) DPG) sufficient to provide 0.3 ppm VM in mash.

2.5% w/v (or about 2.7% by wt,) of 2:1 Ethanol:DPG (3.75 g VM+59.25 g (75 ml) Ethanol+76.65 g (75 ml) DPG) sufficient to provide 0.47 ppm VM in mash VM dissolved in ethanol significantly reduced amount of lactic acid produced. In fact, it appears the VM dissolved in ethanol substantially reduced the *lactobacilli* concentration, and the bacteria did not recover in the 48 hour test. This phenomena was observed in several tests. On many tests data is skewed because low amounts of VM were added. This is particularly significant because the amounts tested, 0.3 to 0.5 ppm VM, are near the lower effective limit of use.

EXAMPLE 7

It was clear that true conditions in poorly mixed industrial fermentators could only be approximated by the smaller bench scale tests described above. Therefore, a test was performed at industrial scale. A formulation "P49" was tested against the control "powdered Lactrol," and results were corrected for minor variations in Brix. The results indicate that by adding solvated VM to poorly mixed industrial fermentators, that lower doses can be administered to get the same response as higher doses of powdered VM.

EXAMPLE 8

It was noted that very high shear could degrade virginiamycin and other similar antimicrobial agents. But adding high concentration (>10% by weight) formulations of virginiamycin in many aprotic solvents resulted in immediate precipitation of the virginiamycin. Adding some surfactants, such as high molecular weight polysorbate (80 units) would help dispersion to some degree. But we also found certain solvents seemed to stay with the virginiamycin, such that dissolution and dispersion was observed, often with little or no precipitation and in the absence of surfactants and dispersants. Solvent combinations which exhibited this feature were ethyl lactate, propylene glycol, dipropylene glycol, ethanol, triethyl citrate and other citrate esters, and mixtures thereof.

It was noted during the evaluation of these systems through HPLC analysis that Ethyl Lactate on its own had a very significant and almost immediate negative impact on VM stability when used to solubilize VM. Comparison of other less aggressive solvents and solvent systems in 1) combination with Ethyl Lactate, 2) in combination with each other, and 3) on their own showed less degradation of VM over time (ie producing a more stable VM solution). It was found that degradation of virginiamycin occurred during storage after the virginiamycin was solvated in various organic solvents. Degradation was highest with very strong solvent. Degradation was also significant with ethyl lactate—12 of virginiamycin would be degraded with a few hours of formulation, and after 56 days only 63% of the original VM would remain. An ethanol/triethyl citrate formulation still had 90% of the original VM present after 56 days, but a 7.5% solution could not be obtained. It was found that certain co-solvents substantially reduced the degradation caused by ethyl lactate. Ethanol seemed most effective at stabilizing solubilized VM in ethyl lactate, and the further addition of even minor amounts (between 0.1 to 0.5 parts triethyl citrate per part ethyl lactate) reduced degradation to minimal levels, e.g, over 80% remaining after 41 days. We believe the triethyl citrate is performing an antioxidant/antihydrolysis function. Formulations of ethanol with triethyl citrate exhibited little or no degradation, but a 6% or 7% by weight virginiamycin solution could not be obtained using only ethanol and virginiamycin.

| Formulation | Wt. % Recovery of VM (Days after formulating) | | | | | | |
|---|---|---|---|---|---|---|---|
| | 1 | 2 | 3 | 4 | 24 | 29 | 42 |
| 5% VM in 1:1 Ethanol:Citroflex 2 | 100 | 100 | 98 | 93 | 95 | 100 | 94 |
| 7.5% VM in Ethyl Lactate | 100 | 94 | 90 | 80 | 79 | 77 | 67 |
| 6% VM in in 1:1 Dipropylene Glycol:Ethyl Lactate | 100 | 99 | 88 | 90 | 94 | 92 | 80 |
| 6% VM in 1:1:0.5 Dipropylene Glycol:Ethyl Lactate:Tween 80 | 100 | 101 | 90 | 102 | 102 | 100 | 88 |
| 6% VM in 1:1:0.5 Dipropylene Glycol:Ethyl Lactate:Citroflex 2 | 100 | 95 | 94 | 87 | 95 | 91 | 84 |
| 7.5% in 1:1:0.5 Ethanol:Ethyl Lactate:Ethyl Acetate | 100 | ND | ND | ND | 83 | ND | 81 |
| 7.5% in 1:1:0.5:0.05 Ethyl Lactate:Ethanol:Citroflex 2:Ethyl Acetate | 100 | ND | ND | ND | 88 | ND | 81 |
| 7.5% in 1:0.44:0.02:0.055 Ethyl Lactate:Ethanol:Ethyl Acetate:Tween 80 | 100 | ND | ND | ND | 86 | ND | 77 |

Interestingly, stability is best enhanced by having the alcohol solvent (ethanol) with ethyl lactate. Surfactants such as polysorbate 80 did nothing to stabilize the VM in a ethyl lactate formulation. Formulas exhibiting both high solubility (~7.5%) and excellent stability (about 80% or VM remaining after 42 days) include formula 93-10, a 7.5% VM in 1:1:0.5 formula of ethyl lactate, ethanol, and triethyl citrate. At 10° C. and at 4° C. storage temperature, more than 92% of VM remains in such a composition after 46 days. Similarly, a composition having 7.5% VM in a 1:1 ethyl lactate/ethanol solution exhibited over 90% stability after 46 days is held at 4° C. or 10° C. A composition having 6% VM in 1:0.2 part solution of ethyl lactate and triethyl citrate. Storage of formulations of of VM in ethyl lactate exhibited poor stability, having only 68% of the original VM remaining after 42 days. Due to the desire to have a VM concentration as high as practicable with a minimum concentration of 7.0% or above needed for commercial viability, focus on formulations containing ethyl lactate as a primary solvent. Ethyl lactate in combination with ethanol, triethyl citrate and/or dipropylene glycol were determined to meet the criteria of having a concentration above 7% while exhibiting significantly better stability characteristics compared to Ethyl Lactate on its own.

Further work was also conducted to evaluate the effect of temperature on the rate of VM degradation in various solvent systems. Stability of various formulations was determined using HPLC at 4° C., 10° C. and 20° C. (Lab ambient conditions). Results showed a significant improvement in VM stability when stored at lower (4 and 10 C) temperatures compared to ambient.

| 7.5% in 1:1:0.5 Ethanol:Ethyl Lactate:Ethyl Acetate | Storage Temp (Precipitate in mm) | | |
|---|---|---|---|
| Formulation Temp | 20° C. | 10° | 4° |
| 15° C. | 3.4 | 1.0 | 4.0 |
| 20° C. | 3.4 | 1.7 | 1.3 |

However, the formulations seem on the border of instability, as at lower temperature some precipitating out of the virginiamycin was noted.

| 7.5% in 1:1:0.5:0.05 Ethyl Lactate:Ethanol:Citroflex 2:Ethyl Acetate | Storage Temp (Precipitate in mm) | | |
|---|---|---|---|
| Formulation Temp | 20° C. | 10° | 4° |
| 10° C. | 0.1 | 9.9 | 12.2 |
| 15° C. | 0.1 | 4.8 | 4.5 |
| 20° C. | 0.1 | 0.1 | 0.1 |

| 7.5% in 1:1:0.5 Ethanol:Ethyl Lactate:Ethyl Acetate | VM (% of original amount remaining) | | |
|---|---|---|---|
| Storage Temp | Day 1 | Day 16 | Day 47 |
| 4° C. | 100 | 91 | 93 |
| 10° C. | 100 | 92 | 91 |
| 20° C. | 100 | 92 | 81 |

TABLE 5

| 7.5% in 1:1:0.5:0.05 Ethyl Lactate:Ethanol:Citroflex 2:Ethyl Acetate | VM % Recovery | | |
|---|---|---|---|
| Storage Temp | Day 1 | Day 16 | Day 47 |
| 4° C. | 100 | 93 | 92 |
| 10° C. | 100 | 90 | 91 |
| 20° C. | 100 | 90 | 73 |

Storage at 10° C. seems optimum, as at 4° C. some virginiamycin will precipitate.

The invention is meant to be illustrated by the examples, and not limited by the examples. A large number of tests were performed that are not shown here as results were deemed duplicative.

What is claimed is:

1. A method of controlling *lactobacilli* metabolism in mash in an ethanol production facility, comprising adding to the mash a treating liquid comprising:

1) ethanol;

2) a $C_1$-$C_4$ alkyl citric acid ester; and 3) a substantially water insoluble pristinamycin antimicrobial agent, a substantially water insoluble polyether ionophore antimicrobial agent, or both, dissolved therein, wherein the term "substantially water insoluble" means the antimicrobial agent has a solubility in pure water at 20° C. of about 0.1 grams per liter or less, and said treating liquid comprises more than 2 grams per liter of said antimicrobial agent(s) dissolved therein.

2. The method of claim 1, wherein the treating liquid is added upstream or within a heat exchanger.

3. The method of claim 1, wherein the substantially water insoluble antimicrobial agent comprises monensin.

4. The method of claim 1, wherein the organic liquid further comprises dipropylene glycol, wherein said treating liquid comprises more than 10 grams per liter of said pristinamycin antimicrobial agent.

5. The method of claim 1, wherein said treating liquid comprises more than 10 grams per liter of said pristinamycin antimicrobial agent.

6. The method of claim 1, wherein the organic liquid further comprises a C1-C4 hydroxycarboxylic acid ester, a C1-C4 alkyl di- or tri-carboxylic acid ester, or both, wherein said treating liquid comprises more than 10 grams per liter of said pristinamycin antimicrobial agent.

7. The method of claim 6, wherein the organic liquid further comprises a C1-C4 alkyl lactate, wherein said treating liquid comprises more than 10 grams per liter of said pristinamycin antimicrobial agent.

8. The method of claim 1, wherein the substantially water insoluble antimicrobial agent comprises a substantially water insoluble pristinamycin antimicrobial agent.

9. The method of claim 1, wherein said treating liquid comprises more than 20 grams per liter of said dissolved pristinamycin antimicrobial agent.

10. The method of claim 1, wherein said treating liquid comprises more than 40 grams per liter of said dissolved pristinamycin antimicrobial agent.

11. The method of claim 1, wherein the substantially water insoluble antimicrobial agent comprises a substantially water insoluble polyether ionophore-type antimicrobial agent, wherein said treating liquid comprises more than 10 grams per liter of said polyether ionophore antimicrobial agent.

12. The method of claim 11, wherein said treating liquid comprises more than 20 grams per liter of said dissolved polyether ionophore antimicrobial agent.

13. The method of claim 12, wherein said treating liquid comprises more than 40 grams per liter of said dissolved polyether ionophore antimicrobial agent.

14. The method of claim 1, wherein the treating liquid consists of ethanol, a C1-C4 alkyl citric acid ester, and virginiamycin.

15. The method of claim 1, wherein the antimicrobial agent is virginiamycin, and wherein the treating liquid further comprises ethanol, a C1-C4 alkyl citric acid ester, and ethyl lactate.

16. The method of claim 1, wherein the treating liquid comprises ethanol, ethyl acetate, ethyl lactate, and triethyl citrate.

17. The method of claim 1, wherein the treating liquid comprises a triethyl citrate ester.

18. The method of claim 1, wherein the treating liquid comprises a triethyl citrate ester and further comprises dipropylene glycol.

19. The method of claim 1, wherein the treating liquid consists essentially of virginiamycin, a triethyl citrate ester and ethanol.

20. The method of claim 1, wherein the treat liquid comprises virginiamycin and the solvents comprise ethanol, ethyl lactate, and triethyl citrate.

* * * * *